(12) United States Patent
Greve

(10) Patent No.: US 11,135,194 B2
(45) Date of Patent: *Oct. 5, 2021

(54) MONOTERPENES FOR TREATING RESPIRATORY DISEASES, IN PARTICULAR BRONCHOPULMONARY DISEASES

(71) Applicant: Maria Clementine Martin Klosterfrau Vertriebsgesellschaft mbH, Cologne (DE)

(72) Inventor: Harald Greve, Düsseldorf (DE)

(73) Assignee: MARIA CLEMENTINE MARTIN KLOSTERFRAU VERTRIEBSGESELLSCHAFT MBH, Cologne (DE)

( * ) Notice: Subject to any disclaimer, the term of this patent is extended or adjusted under 35 U.S.C. 154(b) by 36 days.

This patent is subject to a terminal disclaimer.

(21) Appl. No.: 15/887,289

(22) Filed: Feb. 2, 2018

(65) Prior Publication Data

US 2018/0153851 A1    Jun. 7, 2018

Related U.S. Application Data

(63) Continuation of application No. 13/062,388, filed as application No. PCT/EP2009/005931 on Aug. 14, 2009, now abandoned.

(30) Foreign Application Priority Data

Sep. 4, 2008   (DE) .......................... 102008045702.7
Sep. 12, 2008  (DE) .......................... 102008047221.2

(51) Int. Cl.
| | |
|---|---|
| A61K 31/352 | (2006.01) |
| A61P 11/06 | (2006.01) |
| A61K 31/35 | (2006.01) |
| A61K 31/045 | (2006.01) |
| A61K 45/06 | (2006.01) |
| A61K 31/137 | (2006.01) |
| A61K 31/573 | (2006.01) |
| A61K 9/48 | (2006.01) |
| A61K 9/00 | (2006.01) |
| A61K 31/522 | (2006.01) |

(52) U.S. Cl.
CPC ............ *A61K 31/35* (2013.01); *A61K 9/0014* (2013.01); *A61K 9/0053* (2013.01); *A61K 9/48* (2013.01); *A61K 9/4825* (2013.01); *A61K 31/045* (2013.01); *A61K 31/137* (2013.01); *A61K 31/352* (2013.01); *A61K 31/522* (2013.01); *A61K 31/573* (2013.01); *A61K 45/06* (2013.01)

(58) Field of Classification Search
CPC .... A61K 31/35; A61K 31/045; A61K 31/352; A61P 11/06
See application file for complete search history.

(56) References Cited

U.S. PATENT DOCUMENTS

| | | | |
|---|---|---|---|
| 4,929,741 A | 5/1990 | Fischli et al. | |
| 5,889,049 A | 3/1999 | Juergens | |
| 6,511,653 B1 | 1/2003 | Britto et al. | |

FOREIGN PATENT DOCUMENTS

| | | |
|---|---|---|
| DE | 4319556 C1 | 12/1994 |
| DE | 4319554 A1 | 3/2002 |
| WO | 9517195 A1 | 6/1995 |
| WO | 2006029142 A2 | 3/2006 |
| WO | 2007066151 A2 | 6/2007 |
| WO | 2008025560 A1 | 3/2008 |

OTHER PUBLICATIONS

Juergens. Inhibitory activity of 1,8-cineol (eucalyptol) on cytokine production in cultured human lymphocytes and monocytes. Pulmonary Pharamcology & Therapeutics 17 (2004) 281-287.*
Dompeling et al. Inhaled beclomethasone improves the course of asthma and COPD. Eur Respir J. 1992, 5, 945-952.*
Norman et al. Drugs of the Future (Spain), Jul. 2000 vol. 25, 693-699 abstract.*
Wittmann et al.. Therapy with expectorants in COPD patients: a double-blind randomized study comparing Ambroxol and Cineol, Atemwegs and Lungenkrankheiten, vol. 24, No. 2, pp. 67-74, Feb. 1998.
Keinan et al., Natural ozone scavenger prevents asthma in sensitized rats, Bioorganic & Medicinal Chemistry, vol. 13, pp. 557-562, 2005.
Fachinformation, Soledum Kapseln forte 200 mg, Fachinfo Service, Rote Liste Service GmbH, Postfach 110171, Berlin, Stand, Aug. 2008.
Juergens et al.. Anti-inflammatory activity of 1,8-cineol (eucalyptol) in bronchial asthma: a double-blind placebo-controlled trial, Respiratory Medicine, vol. 97 (3), pp. 250-256, Abstract, Mar. 2003.
Dhand, Pressurized aerosols in the treatment of bronchial asthma, Bulletin Postgraduate Institute of Medical Education and Research Chandigarh, vol. 18, No. 4, pp. 158-163, 1984.

* cited by examiner

*Primary Examiner* — Theodore R. Howell
(74) *Attorney, Agent, or Firm* — Edward E. Sowers; Brannon Sowers & Cracraft PC

(57) ABSTRACT

The invention relates to the combined use of at least one monoterpene which can be applied systemically, in particular perorally, and at least one respiratory tract therapeutic agent which can be applied topically, in particular through inhalation, for the prophylactic and/or therapeutic treatment, in particular combination therapy and/or co-medication, of respiratory tract diseases, in particular bronchopulmonary diseases. Through the combined use of the systemic monoterpene with the topical, in particular inhaled respiratory tract therapeutic agent, the effect or efficiency of the topical or inhaled respiratory disease therapeutic agent can be increased significantly, in particular in a synergistic manner, on the one hand, and the required dosage thereof can be reduced significantly on the other hand, combined with the resulting advantages (e.g., avoidance or reduction of side effects).

17 Claims, 7 Drawing Sheets

MONOTERPENES FOR TREATING RESPIRATORY DISEASES, IN PARTICULAR BRONCHOPULMONARY DISEASES

CROSS-REFERENCES TO RELATED APPLICATIONS

This patent application is a continuation of U.S. application Ser. No. 13/062,388, entitled "MONOTERPENES FOR TREATING RESPIRATORY DISEASES, IN PARTICULAR BRONCHOPULMONARY DISEASES" filed on Jul. 5, 2011, which claims priority to PCT/EP 2009/005931, filed Aug. 14, 2009, and to German Applications DE 10 2008 045 702.7, filed Sep. 4, 2008, and DE 10 2008 047 221.2 filed Sep. 12, 2008, and incorporates all by reference herein, as if each one were independently incorporated in its entirety.

BACKGROUND OF THE INVENTION

The present invention relates to the medicinal field of respiratory disorders, in particular bronchopulmonary disorders, and to their treatment.

The present invention relates in particular to the joint use of, firstly, systemically, in particular orally, administrable monoterpenes together with, secondly, topically, in particular inhalatively, administrable respiratory therapeutics for the prophylactic and/or therapeutic treatment, in particular combination therapy or comedication, of respiratory disorders or bronchopulmonary disorders.

The present invention furthermore relates to a combination therapeutic, in particular in the form of a kit, or a combination therapy for prophylactic and/or therapeutic treatment of bronchopulmonary disorders or respiratory disorders using a comedication of, firstly, systemically administrable, in particular oral, monoterpenes and, secondly, topically administrable, in particular inhalative, respiratory therapeutics.

The term respiratory disorders is to be understood as meaning a general term which refers to all, in particular inflammatory, disorders of both the upper and the lower respiratory tracts and which encompasses both acute and chronic disease states. Examples of respiratory disorders of the upper respiratory tract are, for example, inflammations of the paranasal sinuses (e.g. rhinosinusitis), and examples of respiratory disorders of the lower respiratory tract are, for example, bronchial asthma, bronchitis and COPD.

The term "bronchopulmonary disorders" is a generic term in particular for all inflammatory and non-inflammatory disorders of the lower respiratory tract (i.e. the bronchial and pulmonary respiratory tracts) including in particular bronchial asthma, bronchitis and also chronic obstructive pulmonary diseases ("COPD"), and, in the context of the present invention, is used synonymously with the term "respiratory disorders of the lower respiratory tract".

Bronchial asthma, often simply referred to as asthma, is a chronic inflammatory disorder of the respiratory tract with chronic bronchial hypersensitivity or hyperreactivity, inflammation of the bronchi and also lack of bronchial clearance, where, as a result of the bronchial obstruction, there may be episodes of respiratory distress, a general distinction being made between non-allergic (intrinsic) and allergic (extrinsic) asthma; in addition, mixed types of allergic and non-allergic asthma and mixed types of asthma and COPD are also known. Depending on the severity and the accompanying disease symptoms, in accordance with the Guidelines of the GINA 2006 ("Global Initiative for Asthma"), the different asthma disease stages are classified as GINA I to IV, stage 1 being intermittent asthma, stage 2 being mild asthma, stage 3 being moderate asthma and finally stage 4 being severe asthma. In the new classification (GINA 2007), the priority is asthma control, and a distinction is thus made between controlled, partially controlled and uncontrolled asthma.

In contrast, bronchitis generally refers to an inflammation of the bronchi, in particular the bronchial mucosa, a distinction being made between acute bronchitis on the one hand and chronic bronchitis on the other. According to the World Health Organization (WHO), chronic bronchitis is defined as cough and ejection on most days during at least three months in two successive years, and it is one of the most frequent chronic disorders world-wide (about 15 to 25%) with consequently great relevance from a health-economical perspective. In the case of chronic obstructive bronchitis, there is a persistent bronchial obstruction which in most cases develops from a chronic bronchitis.

The term chronic obstructive pulmonary disease or COPD is used as a collective term for chronic obstructive bronchitis and pulmonary emphysema, the term "obstructive" being the typical feature of persistent bronchial constriction. Classification depends on the severity and the accompanying disease symptoms and is in accordance with the GOLD guidelines (GOLD=Global Initiative for Chronic Obstructive Lung Disease) as the different COPD disease stages from GOLD I to IV.

In the treatment of bronchopulmonary disorders, in particular of respiratory disorders of the type mentioned above, in cases of mild to moderate severity use is frequently made of topical or local, in particular inhalative or inhalable, respiratory therapeutics. These include, for example, inhalative bronchodilators and bronchospasmolytics, such as inhalative beta-2-sympathomimetics, inhalative anticholinergics, inhalative corticosteroids or the like. Owing to their only topical or local action, the inhalative respiratory therapeutics mentioned above are frequently not capable of deploying the desired therapeutic action, so that in most cases relatively high doses have to be administered to achieve the desired therapeutic results, or else in more serious cases systemic therapeutics, in particular based on corticosteroids, have to be co-administered when required or even on a permanent basis. As a consequence of the high doses used and required, in many cases unwanted side-effects are observed, too. Occasionally, an insufficient sensitivity of the abovementioned inhalative respiratory therapeutics with respect to the respiratory disorders to be treated is observed. Finally, a purely topical, in particular inhalative, therapy of the abovementioned respiratory disorders is associated in particular with the disadvantage that the use of inhalative respiratory therapeutics does not always result in sufficient deposition in the peripheral respiratory tract since the smallest branches of the respiratory tract, such as, for example, terminal and respiratory bronchioli, can, in general, not be reached by inhalative therapy, in particular when pulmonary function is reduced, such as, for example, in severe COPD.

Thus, for example, both for bronchial asthma and for COPD—in addition to a basic therapy with bronchodilators—topical or local, in particular inhalative or inhalable, corticosteroids are used from a certain degree of severity. In addition, for severe bronchial asthma according to GINA IV, systemic, in particular oral, corticosteroids are additionally employed.

Inhalable or inhalative corticosteroids, in particular inhalable or inhalative glucocorticoids, synonymously also referred to as "inhalative corticosteroids" or simply by the acronym "ICS", belong to the most important therapeutics for the topical or local, in particular inhalative, treatment of inflammatory respiratory disorders, in particular for bronchial asthma and COPD. The principle of action in the case of regular inhalation consists in a primarily topical or local deposition in the respiratory tract, combined with a simultaneous effective anti-inflammatory action by relatively small amounts of steroids.

On a local or topical level, inhalable corticosteroids, in particular glucocorticoids, reduce respiratory inflammation by inhibition of cytokines and arachidonic acid metabolites (AA metabolites) which are released from activated respiratory epithelial cells and distal macrophages lining the respiratory tract, i.e. alveolar macrophages. Depending on the noxious substance inhaled and the genetic disposition, facilitated by the different chemotactically and vasodilatorily acting mediators mentioned above, various white blood cells enter the respiratory tract causing either eosinophile infiltration in the case of bronchial asthma or primary granulocyte infiltration in the case of COPD. This cell infiltration is known to be an important determinant in the development of respiratory inflammation in bronchial asthma and bronchitis.

However, according to current international and national therapy guidelines, ICS are not employed during early stages of respiratory disorders, but in particular only for mild persistent asthma (GINA II) and for moderate to severe COPD (GOLD III and IV), where in most cases continuous therapy is required [cf., for example: (1) Global Initiative for Chronic Obstructive Lung Disease, GOLD 2004, National Institute of Health NIH and National Heart, Lung and Blood Institute NHLBI, Bethesda, USA, www.goldcopd.com; (2) National Institutes of Health (Ed.), Global Strategy for Asthma Management and Prevention, NHLBI/WHO Workshop Report, Bethesda, USA, U.S. Department of Health and Human Services, 2002, Global Initiative for Asthma, GINA 2004, www.gina.com; (3) British Thoracic Society, The British Guidelines on Asthma Management. Asthma in Adults and Schoolchildren, Thorax 2003, 58: 1-94; (4) R. Buhl et al., Leitlinie zur Diagnostik und Therapie von Patienten mit Asthma [Guideline for the diagnosis and therapy of asthma patients], Deutsche Gesellschaft für Pneumologie and Beatmungsmedizin, Pneumologie 2006, 60: 139-183]. This acknowledged therapeutic strategy takes into account the increasingly known side-effects of ICS and also an insufficient sensitivity of ICS in COPD. For this reason, therapy with ICS is reserved for moderate and severe COPD, this treatment not being able to influence the progression of COPD, however, but rather only being able to reduce exacerbations (cf., for example: B. R.

Celli, Chronic Obstructive Pulmonary Disease: From Unjustified Nihilism to Evidence-Based Optimism, Proc. Am. Thoracic Soc. 2006, 3: 58-65).

Naturally, for the clinical success of a topical therapy with inhalative corticosteroids, in particular glucocorticoids, the degree of deposition and in particular also the distribution of the steroids in the peripheral respiratory tract is of direct relevance. But even if various respiratory aids for metered aerosols and powder preparations are used optimally, the success of the therapy is limited not only by the ability of the patient to inhale optimally, but rather primarily by the principle of inhalation as a consequence of the insufficient treatment of the peripheral respiratory tract. Significant causes of this are thus insufficient steroid deposition in the smallest branches of the respiratory tract ($<10^{-8}$ mol/l) and the associated higher deposition of steroids on the mucous membranes of the mouth and the trachea. As a result thereof, following bioadsorption, relatively small amounts of steroids frequently involuntarily also end up in the blood stream causing typical steroid side-effects such as, for example, inhibition of cortisol production, development of osteoporosis, cataract formation, etc. These side-effects, which are becoming increasingly known, have therefore until now limited the therapeutic use of ICS for milder forms of COPD, although according to the therapy guidelines ICS are, depending on the severity of the respiratory disorder, recommended at even higher dosages and in combination with other therapeutics including oral glucocorticoids for a period of two to three weeks. The actual cause of this is the insufficient deposition of ICS in the peripheral respiratory tract and, at least in COPD, a non-steroidal anti-inflammatory therapy which is additionally required. As yet, the smallest branches of the respiratory tract, such as terminal and respiratory bronchioli, have only been able to be reached by a systemic therapy.

In addition to the therapeutic approaches mentioned above, more or less traditionally, ethereal oils or oil mixtures are also used inhalatively for a relatively short period of time for the symptomatic treatment of, for example, bronchitic conditions and to facilitate expectoration in cases of hypersecretion, in particular for colds. However, this is a therapy which does not address the causes and which is used in particular only for mild, especially acute, respiratory disorders and can be used for chronic and in particular severe respiratory disorders only in a supportive manner, if at all.

The publications DE 43 19 554 C2, DE 43 19 556 C2 and WO 94/28895 A2, which belong to the same patent family, describe a combination therapy with, firstly, orally administered terpene compounds, in particular 1,8-cineol or menthol, and, secondly, likewise systemic, in particular orally administed corticosteroids for the anti-inflammatory treatment of chronic bronchial asthma requiring systemic steroids ("GINA IV"), where the use of the orally administered terpene compounds in the context of a continuous therapy is meant to reduce the need for systemic corticosteroids. However, the administration of systemic corticosteroids is associated with serious side-effects. Owing to these serious side-effects of systemic corticosteroids, the combination therapy described therein is limited to serious forms of bronchial asthma ("GINA IV"). These publications neither describe any inhalative treatment concepts, nor, because of the degree of severity of the disorders treated therein, are they even taken into consideration.

As a consequence, the prior-art treatment methods of bronchopulmonary disorders or respiratory disorders often do not give the desired therapeutic result, or only with unwanted side-effects. In particular, the topical or local, in particular inhalative or inhalable, respiratory therapeutics used according to the prior art (such as, for example, ICS) do not always have the desired therapeutic effect.

BRIEF SUMMARY OF THE INVENTION

Accordingly, it is the object of the present invention to avoid at least some of the above-described disadvantages of the prior art, or at least to reduce them.

In particular, in the context of the present invention, an improved and/or more efficient therapy for the treatment of respiratory disorders, in particular bronchopulmonary disorders, is to be provided.

Furthermore, in the context of the present invention, an improved efficacy or a broader application spectrum is to be enabled or achieved locally or topically, in particular inhalatively administrable respiratory therapeutics of the type mentioned above (such as, for example, inhalative bronchodilators and/or bronchospasmolytics including sympathomimetics, phosphodiesterase inhibitors, parasympatholytics and/or vagolytics, anticholinergics, corticosteroids etc.).

Surprisingly, the applicant has now found that the object illustrated above can be achieved by using, in the context of a comedication, firstly systemically, in particular orally, at least one monoterpene (=systemically administrable component) and, secondly,—together or in combination therewith—at least one topically administrable, in particular inhalative, respiratory therapeutic (=topically administrable component) for the prophylactic and/or therapeutic treatment of respiratory disorders, in particular bronchopulmonary disorders.

Entirely unexpected in this context is in particular the fact that, in the context of the present invention, a systemic, in particular orally administered monoterpene is capable of any interaction with a respiratory therapeutic which, in distinction thereto, is administered only locally or topically, in particular inhalatively, and is additionally then also capable of enhancing the activity of the latter in an unexpected manner, preferably in a synergistic manner. In this way, it is possible to increase the efficacy of the topical, in particular inhalative, respiratory therapeutic, and it is therefore possible to significantly reduce the administered dose thereof, combined with the associated advantages (for example avoidance or reduction of side-effects etc.).

Accordingly, the present invention provides—according to a first aspect of the present invention—the use of, firstly, at least one systemically administrable, in particular oral, monoterpene and, secondly, at least one topically administrable, in particular inhalative, respiratory therapeutic for the prophylactic and/or therapeutic treatment, in particular combination therapy and/or comedication, of respiratory disorders, in particular bronchopulmonary disorders.

In other words, the present invention provides the use of, firstly, at least one monoterpene and, secondly, at least one respiratory therapeutic for the prophylactic and/or therapeutic treatment, in particular combination therapy or comedication, of respiratory disorders, in particular bronchopulmonary disorders, where the monoterpene is administered systemically, in particular orally, and the respiratory therapeutic is administered topically, in particular inhalatively.

As demonstrated, surprisingly, by studies of the applicant, by using a systemic, in particular oral, monoterpene in a combination therapy with a topical, in particular inhalative, respiratory therapeutic in the context of the prophylactic or therapeutic treatment of respiratory disorders, in particular bronchopulmonary disorders, the efficiency or activity of the topical or inhalative respiratory therapeutic can be enhanced significantly, in particular in a synergistic manner. It is completely surprising and was not to be expected that the systemically, in particular orally, administered monoterpene is capable of enhancing the activity or efficiency of the topical or inhalative respiratory therapeutic in the manner found, since two entirely different, separate types of administration—namely systemic on the one hand and locally or topically on the other hand—are used for the two active compounds to be combined (i.e. monoterpene on the one hand and respiratory therapeutic on the other hand).

This effect, discovered completely unexpectedly by the applicant, can possibly—without wishing to adhere to a certain theory—be attributed to the fact that systemic or oral administration of the monoterpene results in a certain amount of the systemically or orally administered monoterpene, in particular owing to diffusion and/or exhalation processes, passing unchanged into the respiratory epithelium, in particular into the alveolar and/or bronchial epithelium, where it is "exhaled", and it is as a consequence found in relatively large concentrations on and in the epithelial cells, where it then encounters the topically or inhalatively administered respiratory therapeutic and can act together with the latter, in particular in a synergistic manner.

As a result of the lipophilicity of the monoterpenes, what is also observed is a long-term storage in the epithelial cells in question, such that a long-term and uniform supply of monoterpenes in the epithelial cells in question is ensured, so that a long-term interaction with the inhalative respiratory therapeutic is ensured.

In the manner described above, it is possible to increase the activity or efficiency of topical or inhalative respiratory therapeutics significantly, in particular in a synergistic manner, and to significantly reduce the employed doses thereof, combined with the associated advantages (for example avoidance or reduction of side-effects etc.). At the same time, by the combined action of, firstly, monoterpene and, secondly, topical or inhalative respiratory therapeutic, the sensitivity to the topical or inhalative respiratory therapeutic can be enhanced significantly; as a consequence, it may be possible to not only reduce the dose of the topical or inhalative respiratory therapeutic, but under certain circumstances also to make the topical or inhalative respiratory therapeutic in question available in the first place for certain respiratory disorders or for certain stages of the respiratory disorders mentioned above, where hitherto it has been impossible to use the topical or inhalative respiratory therapeutics in question owing to the lack of sensitivity.

For its part, the activity enhancement of the topical or inhalative respiratory therapeutic as such can probably—again without wishing to adhere to a certain theory—be attributed to the steroid-like activity potential, surprisingly found by the applicant, of the systemically employed monoterpenes, in particular with respect to the inhibition of inflammation mediators which are formed by various infectious, allergic and/or inflammatory stimuli and—owing to mucus hypersecretion—effect an increase or exacerbation of the respective respiratory inflammation. As precursors of phytosteroids, isolated monoterpenes (such as, for example, 1,8-cineol, menthol etc.) thus have a steroid-like activity potential; that is, they inhibit inflammation mediators. In contrast, complete ethereal mixed oils stimulate prostaglandin production and show a reduced inhibition of leukotriene and cytokine production compared to the dominating monoterpene as main fraction of the mixed oils in question; this is because the mixed oils also comprise substances which stimulate cell activity and mediator production and thus do not act in an anti-inflammatory manner but may cause incompatibility reactions, so that, as a consequence, ethereal mixed oils and oil mixtures generally increase cell activity and induce mediator production and mucus formation. In contrast, however, isolated monoterpenes inhibit mucus hypersecretion by inhibiting mediator production; this is to be considered not as a secretolytic, but rather an anti-inflammatory, in particular mucolytic, effect in the respiratory tract. These effects are—in contrast to inhalative respiratory therapeutics (for example ICS) on their own or as a monotherapeutic—achieved in the entire respiratory tract, in particular in the entire lung, i.e. including the periphery and the alveoli, only when monoterpenes are used. This is because monoterpenes, following systemic administration, in particular in the form of enteric capsules which dissolve in the small intestine, are taken up into the bloodstream and, in accordance with their physical properties, released in the alveoli and thus pass into the exhaled air. As a consequence, monoterpenes are capable of mediating an anti-inflammatory action even in the smallest peripheral branches of the respiratory tract—in contrast to inhalative respiratory therapeutics on their own.

Based on the findings described above, the applicant has, surprisingly, for the first time succeeded in providing an efficient combination therapy for the prophylactic and/or therapeutic treatment of respiratory disorders, in particular bronchopulmonary disorders, which proposes or realizes, in the context of a comedication, the joint use of, firstly, at least one monoterpene which is to be administered systemically, in particular orally, and, secondly,—in combination therewith—at least one respiratory therapeutic to be administered topically, in particular inhalatively.

It is to be understood that, in the preceding description and in the description that follows of the present invention, embodiments made for only one aspect of the invention do, of course, also apply to the other aspects of the invention, without this requiring explicit mention.

It is furthermore understood that, below, all stated amounts, doses and ranges are to be understood such that, if required, in particular for individual cases or relating to certain applications, one may deviate therefrom without leaving the scope of the present invention. This is at the discretion of the person skilled in the art.

The person skilled in the art is aware that, in the context of the combination therapy according to the invention or in the context of the use according to the invention, firstly, the monoterpene to be administered systemically, in particular orally, and, secondly, the respiratory therapeutic to be administered topically, in particular inhalatively, can be administered at the same time or else at different times. Both with a view to the systemic component and with a view to the topical component, in each case a single daily dose may be suitable, or else it may be preferred to divide the respective total daily doses into two or more individual administrations over the course of the day; the decision is at the discretion of the person skilled in the art.

With respect to the monoterpene employed, this may be selected in particular from mono- and bicyclic monoterpenes, preferably from the group consisting of monocyclic monoterpene alcohols, preferably menthol (for example L-menthol), and bicyclic epoxy-monoterpenes, preferably limonene oxides, preferably 1,8-cineol, and also mixtures thereof, particularly preferably from the group consisting of menthol and 1,8-cineol. Very particular preference according to the invention is given to using the monoterpene 1,8-cineol.

It has been found to be particularly effective according to the invention to use the monoterpene as an isolated or single active substance (i.e. not to use a mixture of different monoterpenes or ethereal oils or oil mixtures), of course together with a suitable pharmaceutical carrier or excipient and optionally together with other customary pharmaceutical auxiliaries and/or additives. However, according to the invention, in principle it is not excluded to use two or more monoterpenes together, in particular as a mixture, although this is far less preferred according to the invention.

The terpenes are a highly heterogenous and very large group of chemical compounds which can be derived biosynthetically from isoprene or isopentenyl units, where the biosynthesis takes place via activated forms of these molecules, namely dimethylallyl pyrophosphate (DMAPP) and isopentenyl pyrophosphate (IPP); the units consist of five carbon atoms ($C_5$ units). More than 8000 terpenes and more than 30 000 of the closely related terpenoids are known. In the systematic classification of Organic Chemistry, the terpenes belong to the lipids (secondary natural products). The common building block of all terpenes is isoprene. The terpenes belong to the secondary plant products.

More than 900 monoterpenes are known. All are synthesized by monoterpene synthases from geranyl pyrophosphate (2,6-dimethyloctane). In the context of the present invention, preference is given to using mono- and bicyclic monoterpenes. Most monocyclic monoterpenes which can be derived from p-menthane have a cyclohexane skeleton, whereas the bicycles carane, thujane, pinane, bornane and fenchane and, more generally, also isobornylane and isocamphane are the most important parent compounds of the bicyclic monoterpenes.

Menthol for its part—synonymously also referred to as 2-isopropyl-5-methylcyclohexanol or else as 5-methyl-2-(1-methylethyl)cyclohexan-1-ol—is a monocyclic monoterpene alcohol, whereas 1,8-cineol—synonymously also referred to as eucalyptol, limonene 1,8-oxide, 1,8-epoxy-p-menthane or else as 1,3,3-trimethyl-2-oxabicyclo-[2.2.2]—octane—belongs to the bicyclic epoxy-monoterpenes, more accurately to the limonene oxides.

In the context of the present invention, the monotergene is usually employed in an oral administration form, preferably in the form of capsules. Particular preference according to the invention is given to the administration of the monoterpene in the form of an oral enteric preparation, in particular capsule, which does, however, dissolve in the small intestine. Very particular preference is given to oral enteric preparations, in particular capsules, which dissolve in the small intestine, and which contain a single monoterpene, preferably 1,8-cineol. Such products are commercially available (for example Soledum® capsules sold by Cassella-med GmbH & Co. KG or Maria Clementine Martin Klosterfrau Vertriebsgesellschaft mbH, Cologne, Federal Republic of Germany).

In general, the monoterpene is employed in effective, in particular pharmaceutically effective, amounts. Here, the dose of monoterpene may vary within wide ranges. Usually, the systemically, in particular orally, administered monoterpene is administered in daily doses of from 100 to 2000 mg/die, in particular from 200 to 1200 mg/die, preferably from 300 to 1000 mg/die. In other words, the monoterpene which is to be administered systemically or orally is generally prepared for administration in a daily dose of from 100 to 2000 mg/die, in particular from 200 to 1200 mg/die, preferably from 300 to 1000 mg/die. It is to be understood that, if required, the person skilled in the art may deviate from the amounts mentioned above for individual cases or relating to certain applications without leaving the scope of the present invention.

According to an embodiment which is particularly preferred according to the invention, the monoterpene to be administered systemically or orally is 1,8-cineol in the form of enteric capsules which dissolve in the small intestine, preferably in daily doses in the range of from 100 to 2000 mg/die, in particular from 200 to 1200 mg/die, particularly preferably from 300 to 1000 mg/die.

The daily doses mentioned above can advantageously be divided into one, two, or more individual administrations.

As illustrated above, in combination with the monoterpene to be administered systemically, in particular orally, a respiratory therapeutic to be applied topically is administered as comedication. Like the monoterpene used in accordance with the invention, in the context of the combination therapy according to the invention the respiratory therapeutic to be administered topically is employed in effective, in particular pharmaceutically effective, amounts, too, where the person skilled in the art selects the respective doses depending on the respiratory disorder which is the subject of the therapy and its severity and depending on the topical respiratory therapeutic used.

In general, the respiratory therapeutic to be administered topically and which is used according to the invention is an inhalative or inhalable respiratory therapeutic.

According to the invention, the term respiratory therapeutic to be administered topically, in particular inhalatively, is to be understood very broadly and emcompasses in particular all medicaments and medicament combinations kown to the person skilled in the art for treating bronchopulmonary disorders or respiratory disorders and which are suitable for topical, in particular inhalative, administration.

In a manner which is preferred according to the invention, the respiratory therapeutic to be administered topically, in particular inhalatively, is selected from bronchodilators and bronchospasmolytics. The term bronchodilators refers to substances which widen or dilate bronchi and bronchioli and, in this manner, reduce respiratory resistance, whereas the term bronchospasmolytics refers to substances which reduce the bronchial muscle tone and in some cases inhibit the release of mediator substances from mast cells and increase mucociliary clearance.

In a manner which is preferred in accordance with the invention, the respiratory therapeutic to be administered topically, in particular inhalatively, is selected from the group consisting of (i) corticosteroids, in particular glucocorticoids; (ii) sympathomimetics, in particular betasympathomimetics, preferably beta-2-sympathomimetics; (iii) phosphodiesterase inhibitors; (iv) parasympatholytics and/or vagolytics; (v) anticholinergics; and also mixtures and combinations of the compounds mentioned above.

In a manner which is very preferred according to the invention, the topical, in particular inhalative, respiratory therapeutic is selected from the group consisting of corticosteroids, in particular glucocorticoids, beta-2-sympathomimetics and anticholinergics and also their mixtures and combinations.

It is to be understood that, in the context of the combination therapy or use according to the invention, combinations of at least two or more topical, in particular inhalative, respiratory therapeutics of the type mentioned above are also considered.

As described above, in accordance with one embodiment of the invention, the topically administrable, in particular inhalative, respiratory therapeutic may be a topical or inhalative corticosteroid, in particular glucocorticoid. The topical or inhalative corticosteroid, in particular glucocorticoid, may in particular be a compound from the group consisting of beclometasone, mometasone, budesonide, flunisolide, fluticasone, triamcinolone and their physiologically acceptable derivatives, in particular salts and esters, and also mixtures and combinations.

The corticosteroids are a group of about 50 steroid hormones formed in the adrenal cortex and also chemically comparable synthetic compounds, all corticosteroids being formed from the starting material cholesterol and having progesterone (delta-pregn-4-ene-3,20-dione) as a common skeleton. According to their biological action and the site at which they are formed, the corticosteroids can be divided into three groups, namely the mineralocorticoids, the glucocorticoids and the androgens. The glucocorticoids preferably used in accordance with the invention thus belong to the corticosteroids.

The doses at which the topical or inhalative corticosteroids, in particular glucocorticoids, are employed may vary within wide ranges. The topical or inhalative corticosteroid, in particular glucocorticoid, is usually administered in daily doses of from 50 to 1000 µg/die, in particular from 75 to 800 µg/die, particularly preferably from 100 to 600 µg/die, or is prepared in particular for administration in a daily dose of from 50 to 1000 µg/die, in particular from 75 to 800 µg/die, particularly preferably from 100 to 600 µg/die. It is to be understood that, if required, the person skilled in the art may deviate from the values mentioned above for individual cases or relating to certain applications without leaving the scope of the present invention.

According to an alternative embodiment, the topical or inhalative respiratory therapeutic may be a sympathomimetic, in particular betasympathomimetic, preferably beta-2-sympathomimetic. According to the invention, particular preference is given to the use of inhalative beta-2-sympathomimetics.

The term sympathomimetics denotes substances which mimic the action of the sympathetic nervous system. Specifically, betasympathomimetics (synonymously also referred to as "betamimetics") act mainly on beta-receptors. Very specifically, the beta-2-sympathomimetics, which are preferred in accordance with the invention, relax smooth muscles (beta-2-receptors) and have brochospasmolytic action.

The inhalative beta-2-sympathomimetics which are preferably employed in accordance with the invention may be either short-acting betamimetics (SABA=short-acting beta agonists) or long-acting betamimetics (LABA=long-acting beta agonists). Examples of short-acting betamimetics (SABA) are in particular albuterol, fenoterol, hexoprenalin, levalbuterol, metaproterenol, orciprenalin, pirbuterol, reproterol, salbutamol and/or terbutalin. Examples of long-acting betamimetics (LABA) are in particular salmeterol and/or formoterol.

According to an alternative embodiment, the topical or inhalative respiratory therapeutic may be an anticholinergic. Anticholinergics are substances which suppress the action of acetylcholine and also have bronchospasmolytic activity. Topical or inhalative anticholinergics which are preferably employed in accordance with the invention are ipratropium, tiotropium and/or their physiologically acceptable derivatives, preferably salts, particularly preferably ipratropium bromide and/or tiotropium bromide.

It is understood by the person skilled in the art that, in the context of the use or combination therapy according to the invention, the topical or inhalative respiratory therapeutics mentioned above may also be combined with one another.

In the context of the use or combination therapy according to the invention, it may furthermore be intended to administer additionally at least one further systemic, in particular oral, active compound. This additional systemic, in particular oral, active compound may be selected in particular from the group consisting of systemic phosphodiesterase inhibitors, in particular theophylline; systemic leukotriene receptor antagonists, in particular montelukast, zaforlukast and pranlukast; systemic corticosteroids; and also mixtures and combinations thereof.

In the context of the use according to the invention, it is possible to treat any bronchopulmonary disorders or respiratory disorders.

In particular, the bronchopulmonary disorder may be an inflammatory or non-inflammatory, in particular inflammatory, disorder of the upper or lower respiratory tract.

Furthermore, the bronchopulmonary disorder may be an inflammatory respiratory disorder, in particular a respiratory disorder which is infection-exacerbated and/or requires steroids for treatment.

For example, the bronchopulmonary disorder may be bronchial asthma or bronchitis.

Furthermore, the bronchopulmonary disorder may be chronic obstructive pulmonary disorder (COPD), in particular a chronic obstructive bronchitis or a pulmonary emphysema.

Furthermore, the bronchopulmonary disorder may be a tobacco smoke-induced, in particular nicotine-induced, acute or chronic respiratory inflammation.

In the context of the use or combination therapy according to the invention, it is also possible to treat early forms of COPD, in particular stage 0 or I according to GOLD, or else early forms of bronchial asthma, in particular stage 0 or I according to GINA.

In the context of the use or combination therapy according to the invention, it is in particular also possible to treat early forms of COPD, in particular stage 0 or I according to GOLD, or else early forms of bronchial asthma, in particular stage according to GINA, and in this manner it is possible to achieve exacerbation prophylaxis before or after exacerbation or prevention or slowing down of the progression of the disease before or after exacerbation.

The present invention furthermore relates to the use of at least one systemically administrable, in particular oral, monoterpene, preferably 1,8-cineol, in particular as described above, for the in particular synergistic enhancement of the activity of at least one topically administrable, in particular inhalative, respiratory therapeutic in the prophylactic and/or therapeutic treatment of respiratory disorders, in particular bronchopulmonary disorders.

Furthermore, according to yet a further aspect of the present invention, the present invention relates to the use of at least one systemically administrable, in particular oral, monoterpene, preferably 1,8-cineol, in particular as described above, for the in particular synergistic enhancement of the anti-inflammatory and/or antioxidative activity of topical, in particular inhalative, corticosteroids, in particular glucocorticoids.

Likewise, according to yet a further aspect, the present invention relates to the use of at least one systemically administrable, in particular oral, monoterpene, preferably 1,8-cineol, in particular as described above, for reducing the dose of topically administrable, in particular inhalative, respiratory therapeutics, preferably inhalative corticosteroids, in the prophylactic and/or therapeutic treatment of respiratory disorders, in particular bronchopulmonary disorders.

Furthermore, according to another aspect of the present invention, the present invention relates to the use of at least one systemically administrable, in particular oral, monoterpene, preferably 1,8-cineol, in particular as described above, for inducing and/or enhancing the steroid-permissive effect of topically administrable, in particular inhalative, respiratory therapeutics, preferably inhalative corticosteroids, in the prophylactic and/or therapeutic treatment of respiratory disorders, in particular bronchopulmonary disorders.

According to a further aspect, the present invention also relates to the use of at least one systemically administrable, in particular oral, monoterpene, preferably 1,8-cineol, in particular as described above, for avoiding or reducing habituation to betasympathomimetics in the prophylactic and/or therapeutic treatment of respiratory disorders, in particular bronchopulmonary disorders, in particular with continuous therapy of all degrees of severity of COPD and bronchial asthma.

Moreover, according to a further aspect, the present invention relates to the use of at least one systemically administrable, in particular oral, monoterpene, preferably 1,8-cineol, in particular as described above, in combination with at least one topically administrable, in particular inhalative, respiratory therapeutic, in particular in combination with an inhalative corticosteroid, for reducing the need for or for replacing systemic corticosteroids or other anti-inflammatory and/or immunosuppressive systemic substances in the prophylactic and/or therapeutic treatment of respiratory disorders, in particular bronchopulmonary disorders.

Furthermore, according to yet a further aspect of the present invention, the present invention relates to the use of at least one systemically administrable, in particular oral, monoterpene, preferably 1,8-cineol, in particular as described above, in combination with at least one topically administrable, in particular inhalative, respiratory therapeutic, in particular in combination with an inhalative corticosteroid and optionally further with an inhalative beta-2sympathomimetic, to optimize the basic therapy of bronchial asthma and COPD.

In the context of the uses according to the invention, it is also possible to treat systemic simultaneously affected organs in all severe forms of COPD.

The use according to the invention likewise serves to modulate and inhibit COPD-dependent and/or COPD-independent ageing processes, in particular with the aim of reducing morbidity, increasing the quality of life and/or life expectancy ("anti-ageing").

Furthermore, in the context of the use according to the invention, the monoterpene, in particular 1,8-cineol, can be used as an inducer of NO-production for the treatment of primary and secondary pulmonary-arterial hypertension (PAH) in COPD and bronchial asthma.

Furthermore, in the context of the use according to the invention, the monoterpene, in particular 1,8-cineol, can be used for improving tissue perfusion and/or microperfusion and also bronchodilation in NO-deficiency situations.

Likewise, in the context of the use according to the invention, the monoterpene, in particular 1,8-cineol, can be used for inducing NO-production in recurrent infections of the upper and lower respiratory tracts or in infection-independent exacerbations, in particular owing to cigarette smoking and/or the action of ozone, or for normalizing noxious substance-dependent or -independent NO-deficiency situations.

Likewise, in the context of the use according to the invention, the monoterpene, in particular 1,8-cineol, can be used as an antioxidant and/or NO-inducer in cigarette smoke-induced organ damage, in particular of the lung, the heart, the brain, the kidneys and the venous and arterial vascular system.

Likewise, in the context of the use according to the invention, the monoterpene, in particular 1,8-cineol, can be used for the combined anti-inflammatory and/or antioxidative therapy of the persistent and/or progressive inflammation of the respiratory tract after cessation of smoking, if appropriate with comedication with other respiratory therapeutics, in particular with the aim of delaying the development of emphysemas, respiratory insufficiency and/or the development of peripheral airway obstructions.

Likewise, in the context of the use according to the invention, the monoterpene, in particular 1,8-cineol, can be used for modulating the entire multiorgan ageing process by virtue of anti-inflammatory and/or antioxidative effects in an early long-term therapy.

The present invention furthermore provides, according to yet a further aspect of the present invention, the use of at least one systemically administrable, in particular oral, monoterpene and at least one topically administrable, in particular inhalative, respiratory therapeutic as combination therapeutic and/or for the purpose of comedication for the prophylactic and/or therapeutic treatment of respiratory disorders, in particular bronchopulmonary disorders.

The present invention yet further provides the use of at least one systemically administrable, in particular oral, monoterpene and at least one topically administrable, in particular inhalative, respiratory therapeutic for preparing a combination therapeutic, in particular in the form of a kit, for the prophylactic and/or therapeutic treatment of respiratory disorders, in particular bronchopulmonary disorders.

Likewise, the present invention also provides a combination therapeutic, in particular in the form of a kit, preferably for the prophylactic and/or therapeutic treatment of respiratory disorders, in particular bronchopulmonary disorders, where the combination therapeutic comprises, firstly, at least one systemically administrable, in particular oral, monoterpene and, secondly, at least one topically administrable, in particular inhalative, respiratory therapeutic, in particular as spatially separate components ("kit-of-parts").

The present invention furthermore also provides a method for treating the human or animal body, in particular a method for the prophylactic and/or therapeutic treatment of respiratory disorders, in particular bronchopulmonary disorders, where at least one monoterpene and at least one respiratory therapeutic are each used in effective, in particular pharmaceutically effective, amounts, where the monoterpene is administed systemically, in particular orally, and the respiratory therapeutic is administered topically, in particular inhalatively.

The present invention yet further provides the use of at least one systemically administrable or administered, in particular oral, monoterpene, preferably 1,8-cineol, for the prophylactic and/or curative treatment of respiratory disorders, in particular bronchopulmonary disorders, in smokers and/or former smokers (i.e. in active as well as passive smokers) and for the preparation of a medicament for the prophylactic and/or curative treatment of respiratory disorders, in particular bronchopulmonary disorders, in smokers or former smokers. Here, the monoterpene can optionally be employed together with at least one topically administrable, in particular inhalative, respiratory therapeutic, in particular as a combination therapy and/or in comedication. For further details concerning this point, reference may be made to the above discussions of the other aspects of the invention.

The present invention likewise provides the use of at least one systemically administrable or administered, in particular oral, monoterpene, preferably 1,8-cineol, for the prophylactic and/or curative treatment of antioxidative and/or anti-inflammatory processes in the human body in particular of smokers or for preparing a medicament for the prophylactic and/or curative treatment of antioxidative and/or anti-inflammatory processes in the human body in particular of smokers. Here, the monoterpene can be employed together with at least one topically administrable, in particular inhalative, respiratory therapeutic, in particular as a combination therapy and/or in comedication. For further details concerning this aspect of the invention, reference may be made to the above discussions of the other aspects of the invention, which also, correspondingly, apply to this point.

Finally, the present invention also provides the use of at least one systemically administrable, in particular oral, monoterpene, preferably 1,8-cineol, for increasing the corticosteroid sensitivity of smokers, in particular in the prophylactic and/or therapeutic treatment of respiratory disorders, in particular bronchopulmonary disorders. Here, the monoterpene can optionally be employed together with at least one topically administrable, in particular inhalative, respiratory therapeutic, in particular as combination therapy and/or in comedication. For further details concerning this aspect of the invention, reference may be made to the above discussions of the other aspects of the invention.

Specifically in the treatment of smokers with a systemic or oral monoterpene, preferably 1,8-cineol, it is possible to control the nicotine-induced effect: this is because oxygen radicals like those formed during smoking reduce corticosteroid sensitivity, which is characteristically low for example in COPD. An additional therapy for smokers, in particular those having bronchopulmonary disorders, such as COPD, with a monoterpene, preferably 1,8-cineol, or else a therapy of smokers or former smokers not having respiratory disorders with 1,8-cineol surprisingly prevents the development of bronchopulmonary disorders, such as, for example, COPD, or, in the case of existing respiratory disorders, reduces exacerbations and a progressive course. Furthermore, specifically 1,8-cineol is also suitable for protection against harmful environmental effects.

Systemic administration of the monoterpene, preferably 1,8-cineol, allows—as discussed below—a significant improvement of pulmonary function, in particular in the context of a combination therapy with inhalative or topical respiratory therapeutics, which can be attributed inter alia to the anti-inflammatory and/or antioxidative action of the monoterpene, preferably 1,8cineol. The systemic monoterpene, preferably 1,8cineol, inhibits the prooxidative actions of topical corticosteroids and for its part mediates a non-steroid-like antioxidative action. As a result, the desired steroid sensitivity is increased, in particular also in cases of reduced steroid sensitivity in COPD. Owing to the exposition of the respiratory tract to inhalative noxious substances, in particular cigarette smoke, the positive effects relate mainly to inhalative steroids.

It is to be understood that, for further details concerning the individual aspects of the invention, reference may be made to the more detailed discussions in connection with the first aspect of the invention, which also, correspondingly, apply to the other aspects of the invention.

DETAILED DESCRIPTION OF THE INVENTION

Figure 1:
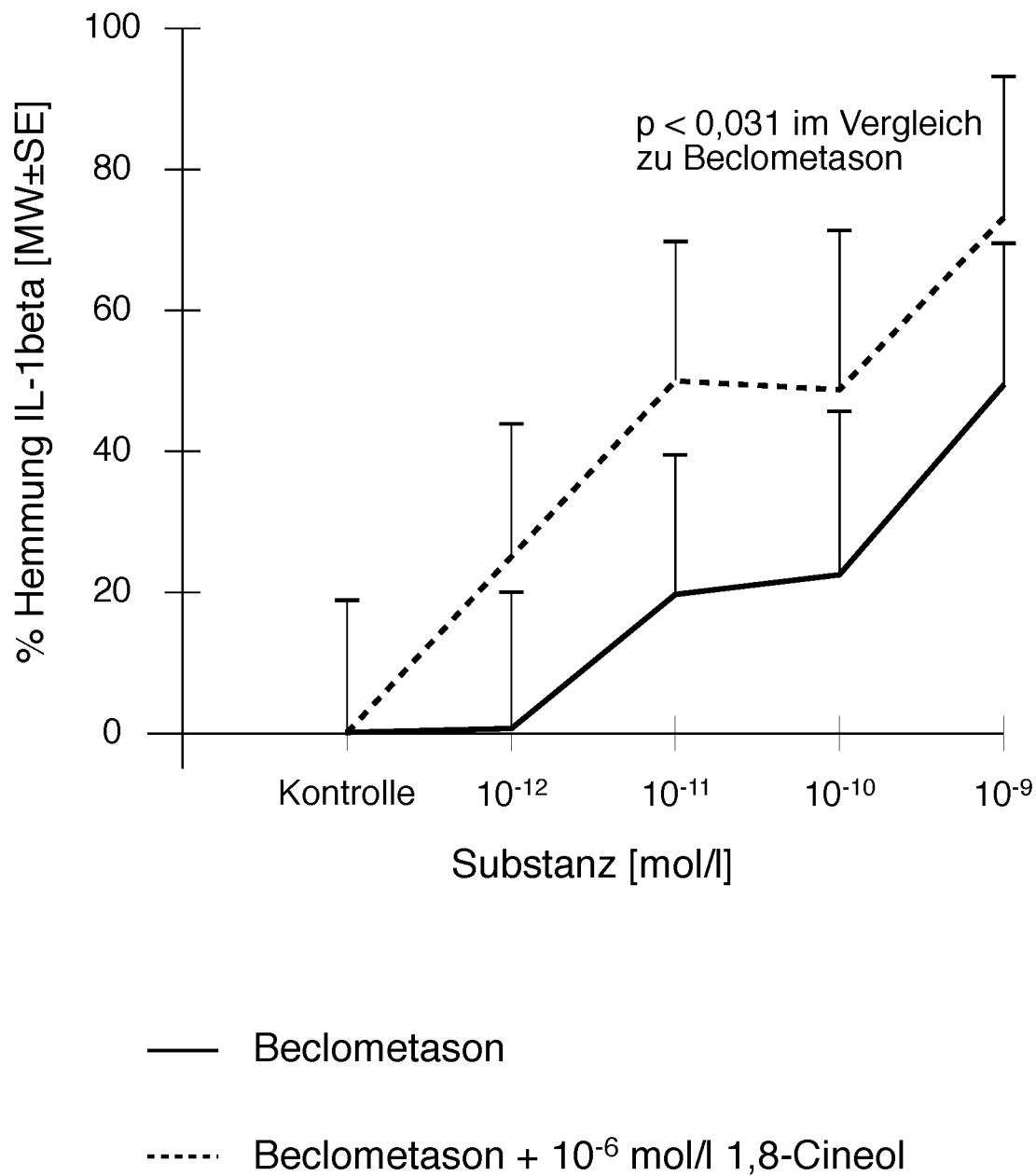
FIG. 1 illustrates the stimulation of the action of the inhalative corticosteroid beclometasone by the monoterpene 1,8-cineol ($10^{-6}$ mol/l) in LPS-stimulated human monocytes in vitro.

In the context of the present invention, there has been found in particular the synergistic anti-inflammatory action of monoterpenes and topical respiratory therapeutics (for example inhalative glucocorticoids).

Particularly surprisingly, as the basis of the present invention, it has been found that therapeutically relevant concentrations of 1,8-cineol significantly increase the anti-inflammatory action of topical respiratory therapeutics, in particular topical glucocorticoids, by synergistic inhibition of the cytokine production. The applicant was able to demonstrate a synergistic anti-inflammatory action of monoterpenes and topical respiratory therapeutics, in particular topical glucocorticoids. Thus, for example, even low therapeutic concentrations of 1,8-cineol (for example $10^{-6}$ mol/l) inhibit the production of IL-lbeta significantly compared to subtherapeutic concentrations of beclometasone, for which, when used on its own, no significant inhibition could be demonstrated. In contrast, by combining 1,8-cineol and inhalative glucocorticoid (beclometasone), a significant inhibition could be demonstrated even for subtherapeutic and therapeutic concentrations of beclometasone with a resulting more intensive action of ICS. More detailed clinical studies show that it is possible to reduce the dose of the inhalative ICS by up to 30% to 50% and more during a systemic long-term therapy with 1,8-cineol (for example Soledum® capsules).

The essential clinical meaning is that the anti-inflammatory action of minimal concentrations, which decrease in the periphery of the lung, of common ICS (metered aerosols and powder preparations) becomes more intensive. The use of the combination according to the invention of systemic monoterpene and topical respiratory therapeutic, in particular topical glucocorticoid, (for example oral 1,8-cineol and ICS or beclometasone) is advantageous in particular in the therapy of a peripheral respiratory inflammation in bronchial asthma and COPD as a novel therapeutic concept and for modulating the steroid-refractory progression of the pulmonary disorder, to prevent the development of irreversible respiratory insufficiency. However, of particular clinical value is the therapeutic use of monoterpenes, in particular 1,8-cineol, for the prophylaxis and therapy of early forms of COPD (GOLD 0 or GOLD I), for which there is currently no anti-inflammatory therapy recommended by all lung associations world-wide.

Furthermore, by a combined therapy of systemic monoterpene and topical respiratory therapeutic, in particular topical glucocorticoid (for example oral 1,8-cineol and ICS or beclometasone), the steroid-refractory respiratory inflammation caused by cigarette smoke and also other harmful proinflammatory or oxidative environmental substances such as, in particular, ozone ($O_3$), and the development of COPD is inhibited prophylactically and/or therapeutically.

A further essential aspect of the present invention is in particular also the prophylactic and alleviating effect of monoterpenes, in particular 1,8-cineol, in combination with topical respiratory therapeutics, in particular topical glucocorticoids, or else of monoterpenes on their own, in particular 1,8-cineol, on inflammations in smokers for the prevention and amelioration of the damage to the respiratory tract caused by cigarette smoke. This damage occurs in particular even many years after smoking cessation or after the action of other noxious substances and is characterized clinically by a progressive obstruction and the development of emphysema with respiratory insufficiency during ongoing antiobstructive therapy.

Especially using the monoterpene 1,8-cineol as additional therapy with modern combined therapy forms (for example ICS plus LABA or ICS in combination with vagolytics or else ICS or SABA on their own), in long-term therapy, surprisingly, in former smokers who had ceased smoking more than ten years previously, an inhibition of the production of INF-α and an increased production of IL-8 in ex-vivo stimulated peripheral human monocytes was found compared to normal monocytes of nonsmokers. From these patients, monocytes were obtained during ongoing therapy with ICS and incubated in vitro with a topical glucocorticoid in a dose-dependent manner. In particular in comparison with a group of normal subjects not undergoing therapy with 1,8-cineol, the results show, with earlier onset, a more pronounced inhibitory action on the production of IL-8 and INF-α in monocytes of patients with COPD. These results lead to the new finding that the inhibition of steroid-sensitive mechanisms alone is not able to have a sufficient effect on the course of the disease, so that a systemic additional therapy with monoterpenes decisively improves persistent respiratory inflammation in COPD, helps to reduce exacerbations in persisting inflammations and in particular in the periphery intensifies the action of smaller concentrations, relevant for the respiratory tract, of topical glucocorticoids or other inhalative respiratory therapeutics.

Currently, the inhibition of exacerbations is one of the most important therapeutic aims in smokers and former smokers suffering from COPD which can be ameliorated by the non-steroidal effects of the monoterpene 1,8-cineol. In addition, 1,8-cineol enhances anti-inflammatory and antiobstructive effects of topical respiratory therapeutics, in particular topical glucocorticoids, so that even hitherto unknown pharmaceutical combinations of, for example, ICS and 1,8-cineol or another monoterpene, LABA and 1,8-cineol, SABA and 1,8-cineol and also of ICS, SABA and 1,8-cineol or of ICS, LABA and 1,8-cineol are suitable as a therapeutical alternative to the therapy of asthma and COPD of all degrees of severity and for the additional treatment of the active systemic component in COPD by the systemic availability of monoterpenes, in particular in capsules which dissolve in the small intestine or as powders.

In the context of the present invention, in the search for the underlying property of monoterpenes, in particular 1,8-cineol, which intensifies anti-inflammatory actions of topical steroids, the applicant has additionally found an antioxidative action of 1,8-cineol due to inhibition of the production of superoxides ($O_2^-$ radicals), the activity of superoxide dismutases (SOD) and of hydrogen peroxide ($H_2O_2$) which as end product of the oxidation stimulates the production of inflammation mediators, in particular of cytokines and arachidonic acid metabolites. Here, for the first time, an inhibition of the spontaneous production of $O_2^-$ radicals was demonstrated at therapeutic concentrations of 1,8-cineol which, at relatively low concentrations relevant for respiratory air, stimulates $O_2^-$ radicals and in the therapeutic range inhibits the production of $O_2^-$ radicals and $H_2O_2$. The cause of these antioxidative actions of 1,8-cineol was surprisingly found to be 1,8-cineol as active inducer of NO production which, via this mechanism, removes $O_2^-$ from the organism as substrate for the formation of NO production. It has thus been found that monoterpenes such as 1,8-cineol actively induce NO production by mediating antioxidative effects. Here, for the first time, it was possible to demonstrate modulating effects of 1,8-cineol for controlling oxidative, cell-damaging and proinflammatory effects by inhibition of $O_2^-$ radicals and a contrary stimulation of anti-inflammatory and vasodilatory NO in the therapeutic range of 1,8-cineol. These results are of integral importance for the prophylaxis and therapy, in particular of pulmonary disorders associated with cigarette smoking, including pulmonary emphysema and the regulation of the tone of pulmonary vessels, and also of damage to greater and lesser circulation. Thus, an increased production of $O_2^-$ radicals is mediated by cigarette smoke, infections, nanoparticles, ozone, allergens and other environmental effects which can be inhibited permanently by a long-term therapy with 1,8-cineol and moreover can be utilized advantageously as a substrate for the production of NO.

NO is known to be an anti-inflammatory mediator, vasodilator, inhibitor of inflammatory mediators, histamine, granulocyte adhesion and platelet aggregation and also as an activator of ciliary function and mucosal clearance and protects comprehensively against respiratory infections and exacerbations of asthma and COPD in all disease stages. In this respect, 1,8-cineol is suitable as a continuous therapeutic which, in chronic bronchitis, COPD, emphysema and rhinosinusitis, by modulation, normalizes and adequately adapts to the respective requirements a suppressed NO production by favourable degradation of $O_2^-$ radicals with induction of NO. This leads in particular to novel indications for the use of monoterpenes, in particular 1,8-cineol, preferably in a relatively high, systemically effective daily dose of, for example, from 600 to 1200 mg, to regulate organ perfusion and to protect the upper and lower respiratory tracts including the lung against noxious substances acting as pathogens, in particular cigarette smoke, respiratory infections and allergic and non-allergic respiratory inflammation in cases of hyperactivity, asthma and rhinitis.

To summarize: the findings discovered in the context of the present invention about monoterpenes lead to a completely new understanding of the group, previously not recognized by the person skilled in the art, of secretolytics and mucolytics including natural ethereal oils or mixed terpenes, ambroxol and N-acetylcysteine, whose use hitherto served primarily to loosen mucus, but not causally to release NO or to modulate other mechanisms and thus not primarily for the prophylaxis and therapy of multifactorial respiratory inflammation. This means that the conventional temporally limited therapy with in most cases ineffective substances targets only actual mucus hypersecretion and that therefore a long-term therapy to prevent the development and progression of respiratory inflammation in COPD and asthma by early use of effective substances with combined antioxidative and anti-inflammatory activity profile and a nonsteroidal anti-inflammatory mechanism of action for enhancing the activity of topical respiratory therapeutics, in particular glucocorticoids, and also good compatibility without steroid side-effects in contrast to the general guidelines of national and international lung associations should be proposed as a matter of urgency. Here, effective substances, such as monoterpenes, in particular 1,8-cineol, may play a more central role in the future owing to their better availability in the respiratory tract as a consequence of their high lipophilicity and the exhalation of the active compound after alveolar uptake from the bloodstream into the pulmonary periphery. Therefore, for monoterpenes, in particular 1,8-cineol, a new classification as belonging to a novel group of substances as "Non-Steroidal Airway Inflammation Modifier (NSAIM)" should be proposed.

Further embodiments, adaptations and variations and also advantages of the present invention are readily discernible and feasible for the person skilled in the art on reading the description, without the person leaving the scope of the present invention. The following working examples serve only to illustrate the present invention, without the invention being limited thereto.

WORKING EXAMPLES

Example 1

In-Vitro Studies

In in vitro studies, it was found that monoterpenes (here specifically: 1,8-cineol) are capable of enhancing the activity of inhalative respiratory therapeutics, in particular glucocorticoids (here specifically: beclometasone), in a significant, in particular synergistic, manner.

Surprisingly, it has been found that therapeutically relevant concentrations of 1,8-cineol significantly enhance the anti-inflammatory action of topical glucocorticoids by synergistic inhibition of cytokine production (see Table 1).

Table 1 shows the synergistic activity of 1,8-cineol ($10^{-6}$ mol/l) and beclometasone on the LPS-stimulated production of IL-1beta in human monocytes in vitro. Monocyte IL-1beta production (n=14-15, 4 experiments) in monocytes is inhibited significantly by cineol ($10^{-6}$ mol/l) compared to the control. Cineol and beclometasone synergistically inhibit IL-1beta production more than beclometasone on its own. Compared to cineol ($10^{-6}$ mol/l) on its own, the IL-1beta production is also inhibited synergistically and to a significantly more pronounced degree by addition of beclometasone ($p<0.05$).

TABLE 1

Synergistic action of 1,8-cineol ($10^{-6}$ mol/l) and beclometasone ("becl.") on the LPS-stimulated production of IL-1beta in human monocytes in vitro

| mol/l | IL-1beta pg/5 × $10^4$ cells | Effect vs. control Inhibition (%) | p Value | Effect vs. cineol $10^{-6}$ mol/l Inhibition (%) | p Value |
|---|---|---|---|---|---|
| control | 5252 ± 1017 | 0 ± 19 | — | — | — |
| cineol $10^{-6}$ | 3548 ± 600 | 32.4 ± 17 | 0.0100 | 0 ± 17 | — |
| beclometasone $10^{-12}$ | 5246 ± 1028 | 0.1 ± 19 | 0.9634 | (+47.8 ± 19) | 0.0100 |
| beclometasone $10^{-11}$ | 4217 ± 864 | 19.7 ± 20 | 0.0596 | (+18.9 ± 20) | 0.5557 |
| beclometasone $10^{-10}$ | 4047 ± 940 | 22.9 ± 23 | 0.0661 | (+14 ± 23) | 0.6945 |

TABLE 1-continued

Synergistic action of 1,8-cineol ($10^{-6}$ mol/l) and beclometasone ("becl.") on the LPS-stimulated production of IL-lbeta in human monocytes in vitro

| mol/l | IL-lbeta pg/5 × $10^4$ cells | Effect vs. control | | Effect vs. cineol $10^{-6}$ mol/l | |
|---|---|---|---|---|---|
| | | Inhibition (%) | p Value | Inhibition (%) | p Value |
| beclometasone $10^{-9}$ | 2654 ± 545 | 49.4 ± 20 | 0.0449 | 25.2 ± 20 | 0.0790 |
| cineol $10^{-6}$ + becl. $10^{-12}$ | 3966 ± 642 | 24.5 ± 16 | 0.1904 | (+11.8 ± 16) | 0.0401 |
| cineol $10^{-6}$ + becl. $10^{-11}$ | 2632 ± 474 | 49.9 ± 18 | 0.0100 | 25.8 ± 18 | 0.0538 |
| cineol $10^{-6}$ + becl. $10^{-10}$ | 2696 ± 607 | 48.7 ± 22 | 0.0088 | 24 ± 22 | 0.0443 |
| cineol $10^{-6}$ + becl. $10^{-9}$ | 347 ± 56 | 93.4 ± 16 | 0.0049 | 90.2 ± 16 | 0.0287 |

The monocyte IL-lbeta production (n=14-15, 4 experiments) in monocytes is inhibited significantly by 1,8cineol ($10^{-6}$ mol/l) compared to the control. 1,8-Cineol and beclometasone synergistically inhibit the IL-lbeta production, more strongly than beclometasone on its own. Compared to cineol (10 mol/l), the IL-lbeta production is also inhibited synergistically and to a significantly more pronounced degree by addition of beclometasone (p<0.05).

Figure 2:
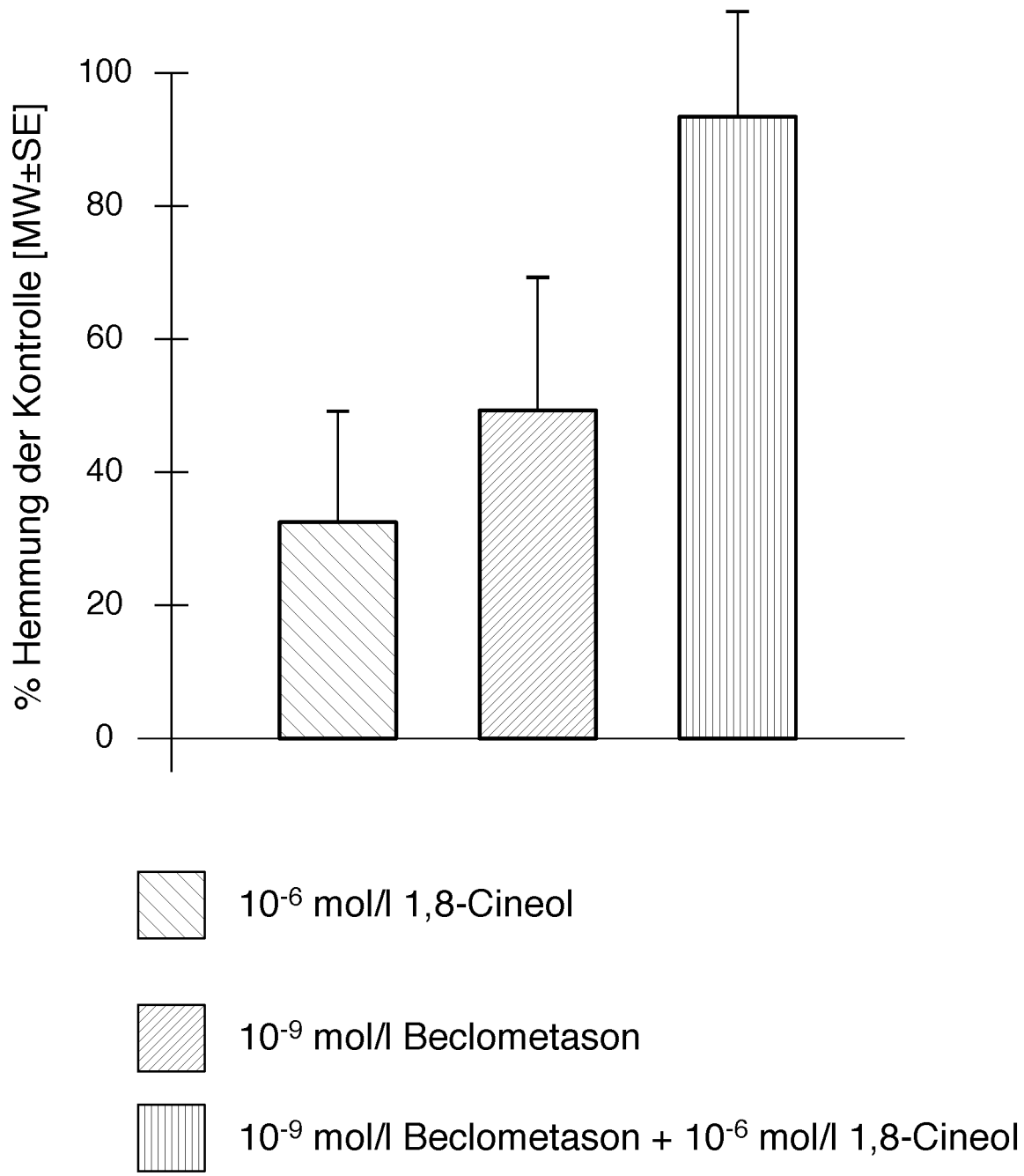
FIG. 2 illustrates the effects of 1,8-cineol on the human inhibition by beclometasone in vitro.

The results from human monocyte cultures show for the first time that the LPS-stimulated production of IL-1beta is inhibited to a significantly more pronounced degree (p<0.01) by beclometasone and 1,8-cineol $10^{-6}$ mol/l (73.4±19%) tahn by beclometasone on its own (49.9±20%) or 1,8-cineol on its own (32.4±17%) (see FIGS. 1 and 2). This is the first demonstration of a synergistic anti-inflammatory action of systemic monoterpenes and topical glucocorticoids.

In this context, FIG. 1 shows the stimulation of the action of the inhalative corticosteroid beclometasone by the monoterpene 1,8-cineol ($10^{-6}$ mol/l) in LPS-stimulated human monocytes in vitro; the addition even of small amounts of 1,8-cineol effects a significant increase of the activity of beclometasone, associated with an increased inhibition of IL-lbeta. FIG. 1 shows the synergistic action of 1,8-cineol and beclometasone: for 20 hours, monocytes (n=14-15, 4 experiments) of healthy subjects ($10^5$/ml) were incubated with 1,8-cineol ($10^{-6}$ mol/l=0.015 µg/ml) and beclometasone ($10^{-12}$-$10^{-9}$ mol/l) in the presence of LPS (10 mg/ml). In cell culture supernatants, the production of IL-1beta was determined by ELISA (from Cayman, AnnArbor, Mich., USA). 1,8-Cineol on its own (−32%±17%, p=0.01) and therapeutically relevant concentrations of beclometasone ($10^{-9}$ mol/l, p=0.045) inhibit the production of IL-1beta. In contrast, the LPS-stimulated production is inhibited to a significantly more pronounced degree (p<0.031) by a combination of 1,8-cineol ($10^{-6}$ mol/l) plus beclometasone ($10^{-11}$-$10^{-9}$ mol/l) than by beclometasone on its own. 1,8-Cineol intensifies in particular the action of subtherapeutic concentrations of beclometasone which are relevant for the peripheral respiratory tract.

FIG. 2 shows the effects of 1,8-cineol on the IL-1beta inhibition by beclometasone in vitro. FIG. 2 likewise illustrates the synergistic action of 1,8-cineol and beclometasone at higher therapeutic concentrations: the LPS-stimulated production of IL1-beta (n=14-15, 4 experiments) is inhibited by therapeutically relevant concentrations of 1,8-cineol in a dose-dependent manner and significantly (p<0.01) compared to the LPS control. The activity of therapeutically relevant concentrations of beclometasone is inhibited significantly (p<0.01) more strongly by 1,8-cineol compared to beclometasone plus 1,8-cineol. To achieve this activity, concentrations of the two substances which are at least 10 times higher have to be present.

Furthermore, the results allow it to be demonstrated for the first time that even low therapeutic concentrations of 1,8-cineol ($10^{-6}$ mol/l) significantly inhibit the production of IL-1beta compared to subtherapeutic concentrations of beclometasone (beclometasone: $10^{-12}$ mol/l: 0%; $10^{-11}$ mol/l: −19.7%±20%; $10^{-10}$ mol/l: −22.9%±13%) for which no significant inhibition was shown. In contrast, by combining 1,8-cineol and beclometasone a significant inhibition could be demonstrated even for subtherapeutic and therapeutic concentrations of beclometasone with a resulting increase in the action of ICS.

These findings confirm the clinical data given below with respect to a significant reduction of the inhalative ICS dose of up to 60% during long-term therapy with oral 1,8-cineol (Soledum® capsules).

A further essential novel aspect of the present data is the prophylactic and alleviating effect of 1,8-cineol in combination with topical glucocorticosteroids or else by 1,8-cineol on its own on inflammations in smokers for the prevention and amelioration of the damage to the respiratory tract caused by cigarette smoke. This damage occurs in particular even many years after smoking cessation or after the action of other noxious substances and is characterized clinically by a progressive obstruction and the development of emphysema with respiratory insufficiency during ongoing antiobstructive therapy. With respect to the recommended combined standard therapies of long-acting beta-2-sympathomimetics (LABA), short-acting beta-2-sympathomimetics (SABA) and inhalative steroids (ICS), novel, hitherto unknown options for additional therapy with 1,8-cineol result, with the aim of enhancing effects of topical therapy and to treat a respiratory disorder now identified as a systemic disorder in a combined manner topically and systemically with additional intensification of the topical anti-inflammatory and bronchodilatatory therapy as systemic disorder by long-term therapy.

Currently, the inhibition of exacerbations is one of the most important therapeutic targets for smokers and former smokers with COPD which can be ameliorated by the non-steroidal effects of the monoterpene 1,8cineol. In addition, 1,8-cineol improves anti-inflammatory and antiobstructive effects of ICS plus LABA, so that hitherto unknown pharmaceutical combination products or kits consisting, for example, of ICS+1,8-cineol or another monoterpene, LABA+1,8-cineol, SABA+1,8-cineol or else ICS+SABA+1,8-cineol or ICS+LABA+1,8-cineol, and also modern combinations with long-acting vagolytics will be suitable in the future as a therapeutic alternative for the therapy of asthma and COPD in all degrees of severity and for the additional treatment of the active systemic component in COPD owing to the systemic availability of monoterpenes in the form of capsules which dissolve in the small intestine or as powders.

In the context of the present invention, for the first time, modulating antioxidative and anti-inflammatory effects of monoterpenes (1,8-cineol) could be demonstrated for controlling oxidative processes and for the induction of nitric oxide production (NO production). In the search for the underlying property of monoterpenes, in particular 1,8-cineol, for the intensification of anti-inflammatory actions of topical steroids, an antioxidative action of 1,8-cineol owing to inhibition of the production of superoxides ($O_2^-$ radicals), the activity of superoxide dismutases (SOD) and of hydrogen peroxide ($H_2O_2$) has been found. Here, for the first time, an inhibition of the spontaneous and stimulated production of superoxides ($O_2^-$ radicals) was demonstrated at therapeutic concentrations of 1,8-cineol, so that the provision of the substrate for the dismutation of $O_2^-$ radicals via a superoxide dismutase activity partially inhibited by 1,8-cineol also inhibited the production of $O_2^-$ radicals and $H_2O_2$ even at low concentrations relevant for the respiratory air and in the therapeutic range. The essential cause of these antioxidative actions of 1,8-cineol was surprisingly found to be 1,8-cineol as active inducer of NO production which, via this additional mechanism, removes $O_2^-$ from the organism as substrate for the formation of NO production. It has thus been found that monoterpenes such as 1,8-cineol actively induce NO production by mediating antioxidative effects. (see Table 2).

Table 2 shows the effect of 1,8-cineol on the PMA-stimulated superoxide production ($O_2^-$ production) (in RPMI 1640) of normal human monocytes in vitro. The dose-dependent effects of 1,8-cineol (4 experiments, n=9-14) on the $O_2^-$ production were measured by determining INT-formazan in culture supernatants (RPMI 1640) of human monocytes ($10^5$/ml) after 20 hours. The $O_2^-$ production was not stimulated by PMA (500 mmol/l). For statistical analysis, the non-parametric Mann & Whitney test was used (p<0.05).

Figure 3:
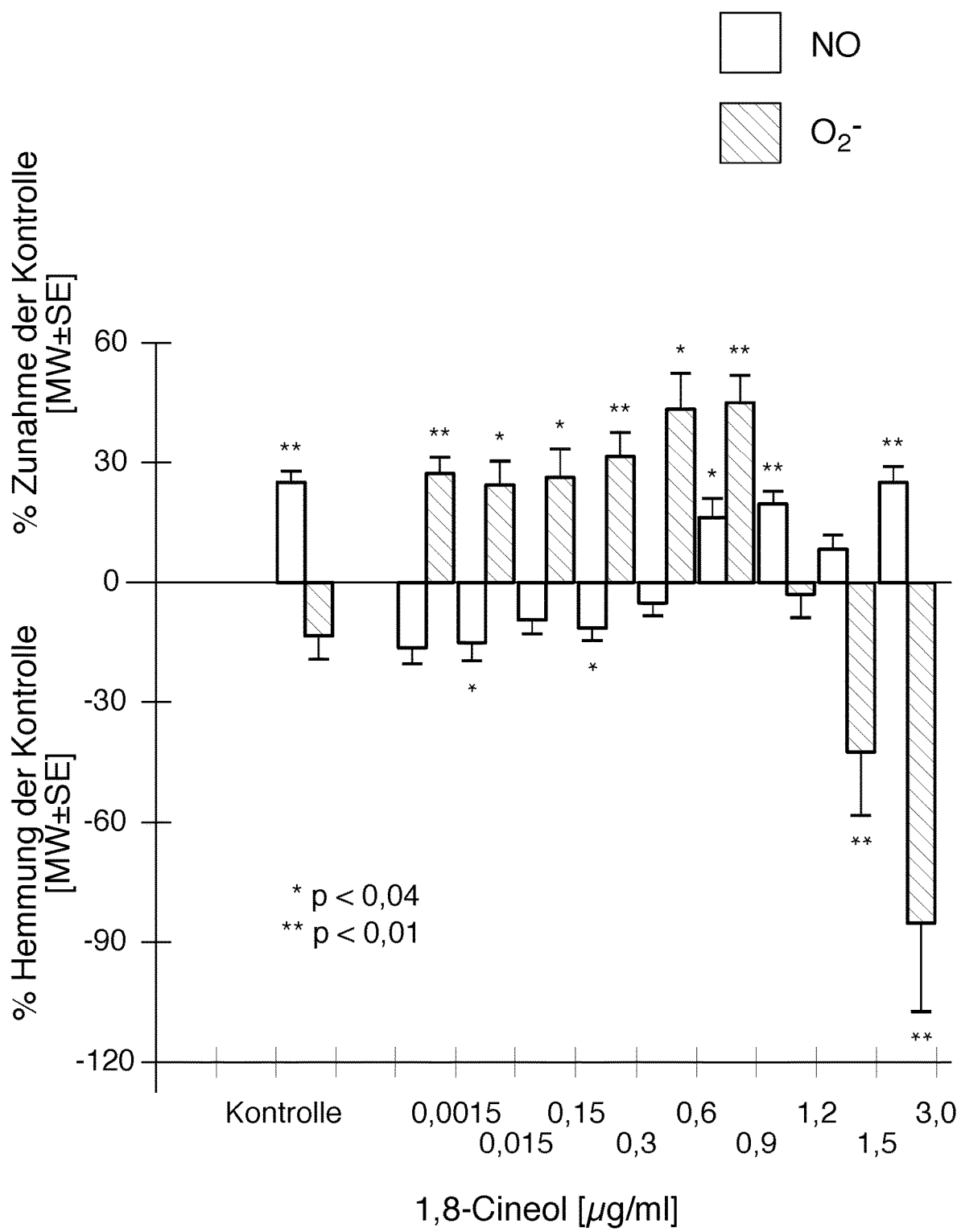
FIG. 3 illustrates the concentration-dependent modulating effects of 1,8-cineol on $O_2^-$ and NO production in stimulated human monocytes in vitro

Here, for the first time, it was possible to demonstrate modulating effects of 1,8-cineol for controlling oxidative, cell-damaging and proinflammatory effects by inhibition of $O_2^-$ radicals and a contrary stimulation of anti-inflammatory and vasodilatory NO in the therapeutic range of 1,8-cineol (see FIG. 3).

TABLE 2

Effect of 1,8-cineol on the PMA-stimulated superoxide production ($O_2^-$ production) in RPMI 1640 normal human monocytes in vitro

| 1,8-Cineol µg/ml (mol/l) | INT-formazan (nmol/$10^5$) | Comparison with control (%) | p Value |
|---|---|---|---|
| spontaneous | 4828 ± 251 | — | — |
| PMA | 4203 ± 267 | −12.9 ± 6 | 0.0990 |
| 0.0015 ($10^{-8}$) | 5.364 ± 229 | +27.6 ± 4 | 0.0083 |
| 0.015 ($10^{-7}$) | 5235 ± 341 | +24.5 ± 6 | 0.0327 |
| 0.15 ($10^{-6}$) | 5327 ± 360 | +26.7 ± 7 | 0.0378 |
| 0.3 (2 × $10^{-6}$) | 5540 ± 359 | +31.8 ± 6 | 0.0091 |
| 0.6 (4 × $10^{-6}$) | 6045 ± 534 | +43.8 ± 9 | 0.0277 |
| 0.9 (6 × $10^{-6}$) | 6107 ± 437 | +45.3 ± 7 | 0.0050 |

TABLE 2-continued

Effect of 1,8-cineol on the PMA-stimulated superoxide production ($O_2^-$ production) in RPMI 1640 normal human monocytes in vitro

| 1,8-Cineol µg/ml (mol/l) | INT-formazan (nmol/$10^5$) | Comparison with control (%) | p Value |
|---|---|---|---|
| 1.2 (8 × $10^{-6}$) | 4099 ± 234 | −2.5 ± 6 | 0.7721 |
| 1.5 ($10^{-5}$) | 2438 ± 389 | −42 ± 16 | 0.0024 |
| 3 (2 × $10^{-5}$) | 634 ± 139 | −84.9 ± 22 | <0.0001 |

FIG. 3 shows the concentration-dependent modulating effects of 1,8-cineol on $O_2^-$ and NO production in stimulated human monocytes in vitro: Following stimulation (20 hours) of normal human monocytes ($10^5$/ml), the production of NO is induced and that of $O_2^-$ is suppressed in the control (i.e. without 1,8-cineol). In contrast, low concentrations of 1,8-cineol slightly induce $O_2^-$ production and, at subtherapeutic concentrations (0.15 µg/ml=$10^{-6}$ mol/l), inhibit the production of NO. In the therapeutic range of 1,8-cineol, the $O_2^-$ production is inhibited strongly in the presence of stimulating effects on the production of NO (*p<0.04, **p<0.01).

These results are of integral importance for the prophylaxis and therapy, in particular, of pulmonary disorders associated with cigarette smoking, including pulmonary emphysema and the regulation of the tone of pulmonary vessels, and also of damage to greater and lesser circulation. Thus, an increased production of $O_2^-$ radicals is mediated by cigarette smoke, infections, nanoparticles, ozone, allergens and other environmental effects, which production can be inhibited permanently by a long-term therapy with 1,8-cineol and moreover can be utilized advantageously as a substrate for the production of NO. NO is known to be an anti-inflammatory mediator, vasodilator, inhibitor of inflammatory mediators, histamine, granulocyte adhesion and platelet aggregation and also as an activator of ciliary function and mucosal clearance and protects comprehensively against respiratory infections and exacerbations of asthma and COPD in all disease stages. In this respect, 1,8-cineol is suitable as a continuous therapeutic which, in chronic bronchitis, COPD, emphysema and rhinosinusitis, by modulation, normalizes and adequately adapts to the respective requirements a suppressed NO production by favourable degradation of $O_2^-$ radicals with induction of NO. This leads in particular to novel indications for the use of monoterpenes, in particular 1,8-cineol, preferably in a relatively high, systemically effective daily dose, to regulate organ perfusion and to protect the upper and lower respiratory tracts including the lung against noxious substances acting as pathogens, in particular cigarette smoke and other emissions or fine dusts, respiratory infections and allergic and non-allergic respiratory inflammations in cases of hyperactivity, asthma and rhinitis. These hitherto unknown properties associated with the action of monoterpenes, in particular 1,8-cineol, may contribute in establishing in the future, for the first time, the additional therapy with 1,8-cineol in the literature and the therapy guidelines.

Example 2

Clinical Results 10 patients 56 to 72 years of age with persistent bronchial asthma (GINA II) treated with a combination therapy of inhalative glucocorticoid (beclometasone, 2×200 µg/die by inhalation) and inhalative long-acting beta-2-sympathomimetics (LABA, salmeterol) and also oral theophyllin were given 1,8-cineol (Soledum® capsules) 4×200 mg/die orally for one week. Even after a one-week therapy at the dose mentioned above, in 8 of the 10 subjects a slight to moderate improvement of lung function was achieved. After continuing therapy for a further twelve weeks, the persistent bronchial asthma had stabilized to such an extent that in 7 of the 10 patients the inhalative glucocorticoid required could be reduced by up to 60% and in 2 of the 10 patients the inhalative glucocorticoids could be discontinued altogether at times. The therapy was tolerated well, without any side-effects. In 5 of the patients treated, the betamimetics required, too, could be reduced by up to 40%.

A further 12 patients 59 to 78 years of age with persistent bronchial asthma (GINA III) treated with a combination therapy of inhalative glucocorticoid (beclometasone, 2×400 µg/die by inhalation) and inhalative long-acting beta-2-sympathomimetics (LABA, salmeterol) and also oral theophyllin were given 1,8-cineol (Soledum® capsules) 4×200 mg/die orally for one week. Even after a one-week therapy at the dose mentioned above, in 9 of the 12 subjects a slight to moderate improvement of lung function was achieved. After continuing therapy for a further twelve weeks, the persistent bronchial asthma had stabilized to such an extent that in 9 of the 12 patients the inhalative glucocorticoid required could be reduced by up to 30%. The therapy was tolerated well, without any side-effects. In 4 of the patients treated, the betamimetics required, too, could be reduced by up to 25%.

The results of the experiments show that monoterpenes significantly increase the efficacy of inhalative respiratory therapeutics, and that it is therefore possible to significantly reduce the amounts thereof which must be administered.

Example 3

Further Clinical Results

In a placebo-controlled double-blind study, the effect of an additional therapy with 1,8-cineol in the form of capsules which dissolve in the small intestine (Soledum® capsules, 3×200 mg/die, oral) on exacerbation rate and lung function was examined in 3 winter months of two successive years using 242 smokers with COPD (GOLD II to III). Both patient groups were identical with respect to age, sex, body mass index, smoker status, lung function and a guideline-conform medication of ICS, LABA, SABA, anticholinergics and theophyllin. In the verum group, the additional therapy with 1,8-cineol led to a significant reduction in the exacerbation rate of −38.5% compared to the placebo group. Additionally, the lung function (FEV1) in the verum group (+5.1%) had improved significantly compared to the placebo group (−1%). Clinical parameters such as the St. George's Respiratory Questionnaire (SGRQ), too, had improved significantly more in the verum group (−10.4 units) compared to the placebo group (−5 units). Thus, the results show, for the first time, that an additional therapy with 1,8-cineol in the form of capsules which dissolve in the small intestine reduces the decrease, reported in the literature, in the frequency of exacerbations by the known combined therapeutic approaches involving budesonide and formoterol (−24%, 13) and fluticasone and salmeterol (−25%, 14) by a further 25%.

Summary and Outlook:

The findings reported above confirm a significant reduction of the inhalative ICS dose of up to 60% during a long-term therapy with oral 1,8-cineol (Soledum® capsules). The essential clinical significance is the intensification of the anti-inflammatory action of minimal concentrations of customary ICS (for example metered aerosoles and powder preparations) which decrease in the periphery of the lung.

The use of 1,8-cineol and ICS is advantageous in particular in the therapy of a peripheral respiratory inflammation in COPD as a novel therapeutic concept and for modulating the steroid-refractory progression of the pulmonary disorder, to prevent the development of irreversible respiratory insufficiency. Of particular clinical value is, for example, the therapeutic use of 1,8-cineol for the prophylaxis and therapy of early forms of COPD (i.e. GOLD 0 or GOLD I), for which there is currently no anti-inflammatory therapy recommended by all lung associations world-wide. Moreover, by a combined therapy of 1,8-cineol and ICS, the steroid-refractory respiratory inflammation caused by cigarette smoke and also other harmful proinflammatory and oxidative environmental substances such as, in particular, ozone ($O_3$), and the development of COPD is inhibited prophylactically and/or therapeutically.

Example 4

Further Tests and Test Data

More detailed in vitro studies of the anti-inflammatory action of 1,8-cineol, in particular in acute colds and/or chronic-obstructive respiratory disorders In vitro studies to determine the effects of an additional therapy with 1,8-cineol and inhaled steroids (ICS) on the production of superoxides ($O_{2-}$) in normal human monocytes Introduction According to the current state of research, the applicant was able to demonstrate antioxidative actions of the active compound 1,8-cineol, in addition to anti-inflammatory actions. The antioxidative action is based primarily on an inhibition of superoxides and an additional action by inhibition of the superoxide dismutase activity (SOD activity), accompanied by a resulting inhibition of hydroperoxides ($H_2O_2$) which act in a proinflammatory manner on the transcription, with formation of cytokines and other inflammation mediators.

Systemic 1,8-cineol, for example in the form of Soledum® capsules, can be employed—as discussed above for example as additional therapy firstly for severe COPD (for example GOLD III/IV) and/or as monotherapy for mild forms (for example GOLD I/II), i.e. also for chronic and acute bronchitis. It appears to be particularly worthy of mention that, for chronic bronchitis, the COPD guideline (GOLD) does not suggest any anti-inflammatory or antioxidative therapy apart from avoidance of noxious substances. This constitutes a gap in the current guidelines which was closed in the context of the present application.

In the more detailed studies of the applicant on 1,8-cineol, it was possible to verify in principle the hypothesis that an additional therapy with systemic 1,8-cineol in correlation with earlier and ongoing clinical studies with Soledum® capsules can mediate a potentiating superior antioxidative and/or anti-inflammatory action by enhancing the mediator inhibition in normal human monocytes.

Since an antioxidative effect of the standard therapy of severe COPD consisting of, for example, LABA plus ICS has hitherto not been known, these newly recognized effects of 1,8-cineol on the inhibition of superoxides compared to ICS and LABA (1,8-cineol vs. ICS and 1,8-cineol plus ICS) have been examined for the first time in the context of the present invention.

Hypothesis and Issues

Firstly, it was an object to examine the antioxidative effects of an additional therapy with 1,8-cineol for inflammatory respiratory disorders (for example COPD or asthma). Since the action of 1,8-cineol as comedication, in particular in combination with inhalative steroids and other guideline recommendations, has hitherto not been known, there is a need to develop novel principles to justify the novel therapeutic approach of using 1,8-cineol for respiratory disorders. Based on this knowledge it is an object to justify the present results of the clinical studies and to establish the strategy of the additional therapy by a new understanding. This is also the base for the examination of novel clinical issues concerning the use of 1,8-cineol.

The additional effect of 1,8-cineol ($4\times10^{-6}$ mol/l and $6\times10^{-6}$ mol/l) is to be tested by co-incubation with therapeutically relevant concentrations ($10^{-11}$ mol/l, $10^{-10}$ mol/l, $10^{-9}$ mol/l) and higher concentrations ($10^{-8}$ mol/l, $10^{-7}$ mol/l, $10^{-6}$ mol/l) of beclometasone ("becl."). Moreover, the effects of beclometasone on its own at the concentrations mentioned is to be determined in comparison to 1,8-cineol. It is intended to test these effects on a combination of 1,8-cineol and beclometasone ("becl.") as standard-ICS on the FCS (fetal calf serum)-stimulated production of $O_2^-$ on normal human monocytes. The aim of the studies is to test additional effects of suboptimal ($4\times10^{-6}$ mol/l) and optimal ($4\times10^{-6}$ mol/l) concentrations of 1,8-cineol on different concentrations of beclometasone.

Methods

In Vitro Method for Determining the Additional Effects of a Co-incubation of 1,8-cineol and beclometasone As already described, monocytes were isolated from 50 ml of venous blood which was repeatedly donated voluntarily for the experiments by healthy non-smoking subjects (n=4). The active compounds beclometasone and 1,8-cineol were diluted with ethanol up to a maximum concentration of 0.01%. The substances were incubated individually (beclometasone $10^{-12}$ to $10^{-6}$ mol/l) and in combination ($10^{-11}$ to $10^{-9}$ mol/l beclometasone with $6\times10^{-6}$ mol/l=0.9 µg/ml 1,8-cineol) and also in an additional series at a 1,8-cineol concentration which is not antioxidatively active ($4\times10^{-6}$ mol/l). To this end, the active compounds were incubated together with freshly isolated monocytes ($10^5$/ml) and the FCS stimulus (10%, from Sigma) for 20 hours in a cell culture medium (RPMI-1640, from Sigma). The culture supernatants were then obtained after treatment of the cell membranes with Triton-X 100 and immediately examined for production of $O_2^-$ radicals.

Analytic Method for the Determination of Superoxides ($O_2^-$) in Culture Supernatants of Human Monocytes The determination of the cytosolic superoxide production is based on the reduction of the dye p-iodonitrotetrazolium violet (INTV), which reacts specifically with superoxide ions, to iodonitrotetrazolium formazan (formazan). INTV is taken up by the cells into the cytosol. Intracellularly, the nitrogen cycle of the INTV is reduced by free superoxide radicals, giving rise to a water-soluble intermediate and the water-insoluble formazan, which have their absorption maxima at 505 and 490 nm, respectively. In contrast, INTV does not absorb light of these wavelengths. At the end of an experiment, the cell lysate is (after treatment with hydrochloric acid) measured at 492 nm in a photometer. Here, the absorption of light is proportional to the amount of intracellularly accumulated INT-formazan which can then be determined using a formazan calibration curve. The INT-formazan accumulation for its part is determined as a measure for the intracellular production of superoxide.

Crossreactions with 1,8-cineol To make sure that true inhibitory effects of 1,8-cineol on the INT-formazan accumulation were present, possible crossreactions of 1,8-cineol with the components of the measurement system were excluded. To this end, beclometasone $10^{-6}$ mol/l, 1,8-cineol $10^{-5}$ mol/l, INTV 0.5 mg/ml and also beclometasone $10^{-6}$ mol/l+1,8-cineol $10^{-5}$ mol/l+INTV 0.5 mg/ml were incubated without cells and the INT-formazan production was measured. Neither 1,8-cineol nor beclometasone on their own or in combination with INTV had any detectable effect on the determination of the INT-formazan production. Crossreactions of 1,8-cineol and beclometasone with the measurement method could therefore be excluded.

Statistical Analyses

Studies on the dose-dependent production of $O_2^-$ radicals in the various issues were carried out in key experiments with beclometasone (Expt. 3, n=10 to 11), 1,8-cineol (Expt. 5, n=12), beclometasone+1,8-cineol $4\times10^{-6}$ mol/l (Expt. 4, n=14 to 15) and beclometasone+1,8-cineol $6\times10^{-6}$ mol/l (Expt. 3, n=11 to 12). Effects of 1,8-cineol and beclometasone are expressed as "% of the FCS control" and were examined statistically using the non-parametric Mann & Whitney test. p values <0.05 are considered to be statistically significant.

Results

Figure 4:
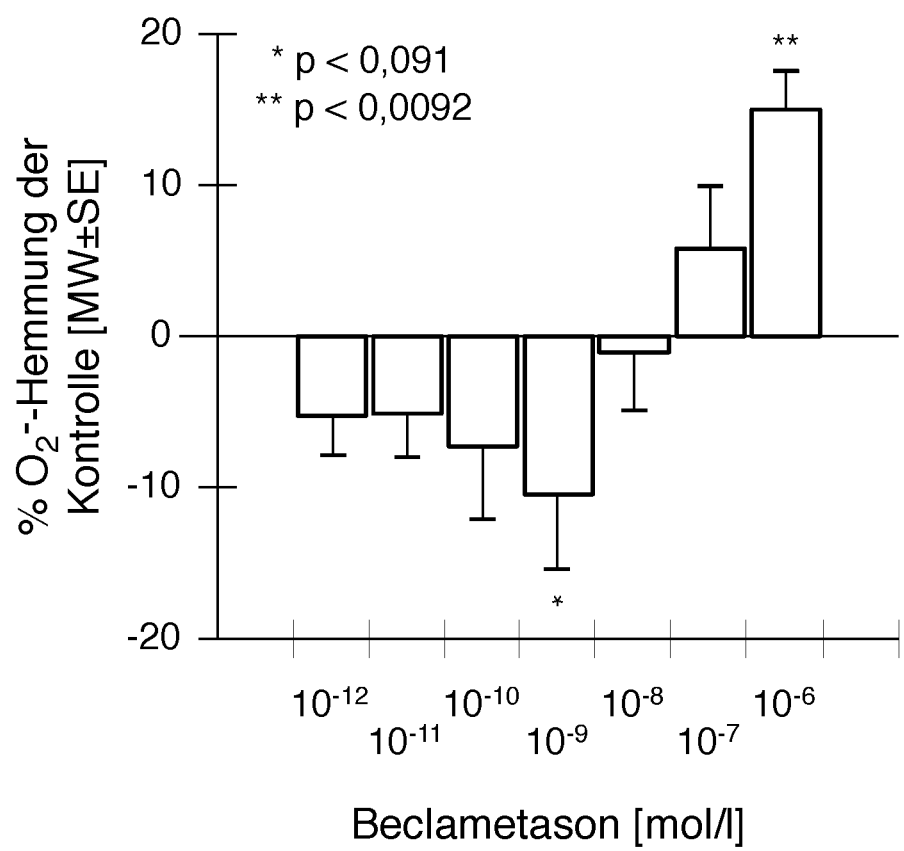
FIG. 4 illustrates the stimulation of monocyte $O_2^-$ production with high concentrations ($\geq 10^{-8}$ mol/l) of beclometasone.

Comparison of the Effects of Beclometasone and 1,8-cineol on the Fetal Calf Serum (FCS)-stimulated Production of Superoxides ($O_2^-$) in Normal Human Monocytes Monocytes ($10^5$/ml) were incubated with different concentrations of beclometasone ($10^{-12}$ to $10^{-6}$ mol/l, n=10-11) for 20 hours together with the FCS stimulus (10%). A borderline significant inhibition (−10.5±5%, p=0.0910) of the $O_2^-$ production was demonstrated only for beclometasone $10^{-9}$ mol/l (see Table 3). High concentrations $10^{-8}$ mol/l) of beclometasone stimulated the monocyte $O_2^-$ production, with a significant increase (15.2±2.5%, p=0.0092) at $10^{-6}$ mol/l (see FIG. 4). Thus, an inhibition of the $O_2^-$ production could not be demonstrated for beclometasone.

Figure 5:
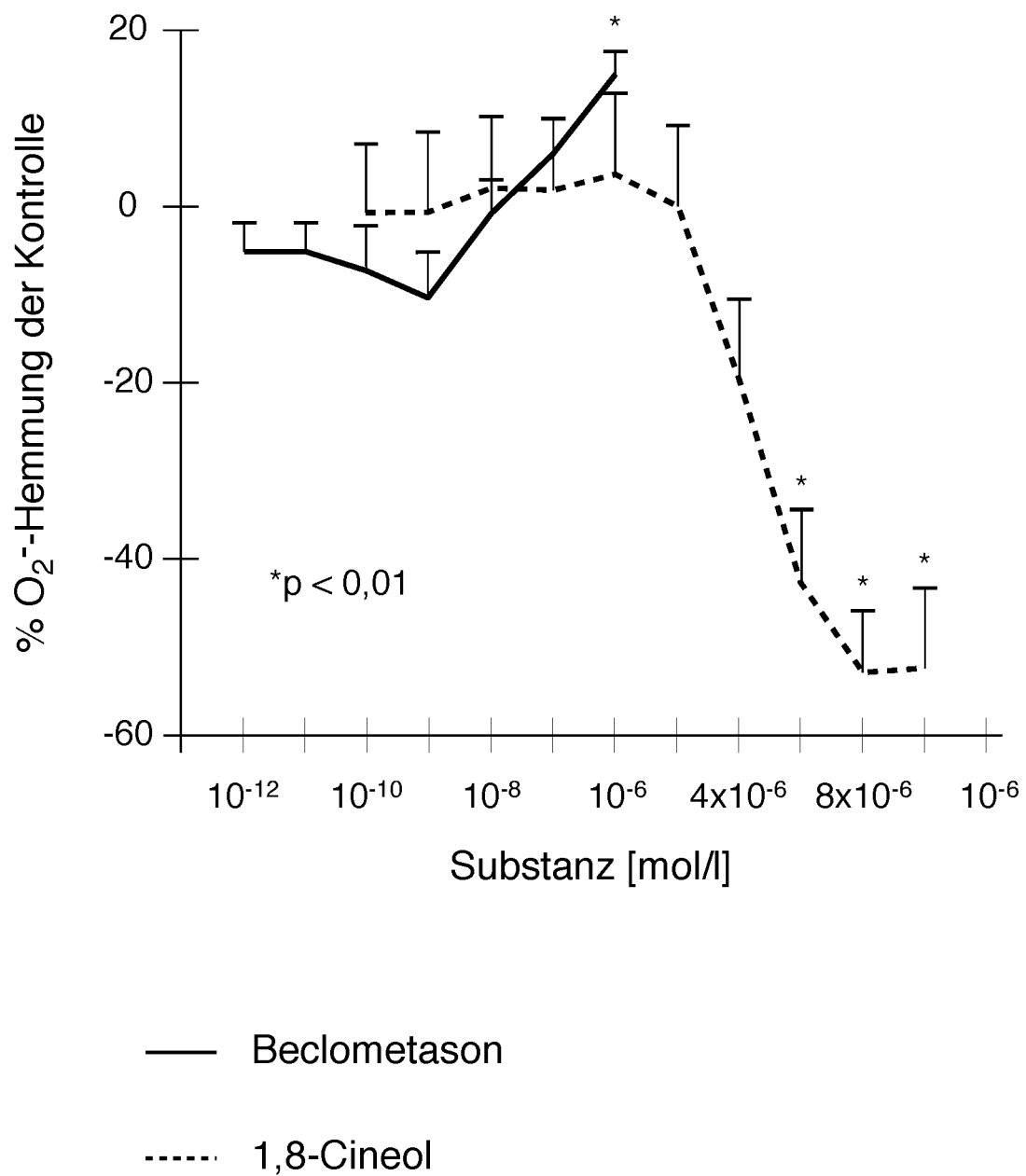
FIG. 5 illustrates the comparative actions of beclometasone and 1,8-cineol regarding the inhibition/stimulation of superoxide ($O_2^-$).

In contrast to the action of beclometasone, a strong inhibition of the $O_2^-$ production (−42.6±8%, p=0.0007) was demonstrated for 1,8-cineol even at a therapeutically relevant concentration (0.9 mg/ml=$6\times10^{-6}$ mol/l). In contrast to beclometasone, which at therapeutic concentrations does not inhibit the $O_2^-$ production and at higher concentrations stimulates the $O_2^-$ production, 1,8-cineol inhibited the $O_2^-$ production in the therapeutic range. The inhibition profile of these different actions of the substances is shown in a comparative manner in FIG. 5.

Effect of a Suboptimal Concentration (0.6 µg/ml) of 1,8-cineol+Beclometasone on the FCS-stimulated Production of Superoxides ($O_2^-$) in Normal Monocytes Owing to the different activity profiles found for beclometasone and 1,8-cineol, additive or synergistic actions of the two substances were investigated. Co-incubations even of a concentration of 1,8-cineol which is itself not yet oxidatively active with beclometasone (n=14-15) were initiated under the experimental conditions described to examine a possible synergistic action of the two substances. The chosen concentration of 1,8-cineol $4\times10^{-6}$ mol/l on its own showed no effect (−9±6%, p=0.2717), and neither did the concentrations of beclometasone examined $10^{-11}$ to $10^{-9}$ mol/l (see Table 5). In contrast to the not significantly inhibiting properties of the individual substances, a likewise not significant borderline increase of the $O_2^-$ production was demonstrated for 1,8-cineol+beclometasone $10^{-10}$ mol/l (2±7%, p=0.7557) and for 1,8-cineol+beclometasone $10^{-9}$ mol/l (4±8%, p=0.8519).

TABLE 3

Effect of beclometasone (becl.) on the FCS-stimulated superoxide production of normal human monocytes in vitro

| mol/l | n | $O_2^-$ (nmol/ml) | Percent of control | p-Value |
|---|---|---|---|---|
| spontaneous | 11 | 8875 ± 429 | — | — |
| FCS 10% | 11 | 15858 ± 550 | — | <0.0001 |
| $10^{-12}$ | 11 | 15050 ± 455 | −5.1 ± 3 | 0.1783 |
| $10^{-11}$ | 11 | 15042 + 568 | −5.1 ± 3 | 0.2643 |
| $10^{-10}$ | 10 | 14702 ± 682 | −7.3 ± 5 | 0.1392 |
| $10^{-9}$ | 10 | 14192 ± 733 | −10.5 ± 5 | 0.0910 |
| $10^{-8}$ | 10 | 16035 ± 639 | −1.1 ± 4 | 0.7513 |
| $10^{-7}$ | 10 | 16782 ± 678 | +5.8 ± 4 | 0.2751 |
| $10^{-6}$ | 10 | 18240 ± 463 | +15 ± 2.5 | 0.0092 |

TABLE 4

Effect of 1,8-cineol on the FCS-stimulated superoxide ($O_2^-$) production of normal human monocytes in vitro

| 1,8-Cineol mg/ml (mol/l) | INT-Formazan (nmol/$10^5$) | Comparison to control (%) | p-Value |
|---|---|---|---|
| spontaneous | 13756 ± 1675 | — | — |
| FCS 10% | 21507 ± 1675 | 56.3 ± 8 | 0.0022 |
| 0.000015 ($10^{-10}$) | 21360 ± 1766 | −0.7 ± 8 | 0.9081 |
| 0.00015 ($10^{-9}$) | 21329 ± 1920 | −0.8 ± 9 | 0.7728 |
| 0.0015 ($10^{-8}$) | 21946 ± 1858 | 2 ± 8 | 0.7508 |
| 0.015 ($10^{-7}$) | 21899 ± 1879 | 1.8 ± 8 | 0.087 |
| 0.15 ($10^{-6}$) | 22286 ± 2036 | 3.6 ± 9 | 0.4884 |
| 0.3 ($2 \times 10^{-6}$) | 21499 ± 1959 | 0.04 ± 9 | 0.9081 |
| 0.6 ($4 \times 10^{-6}$) | 17240 ± 1637 | −19.8 ± 9 | 0.0833 |
| 0.9 ($6 \times 10^{-6}$) | 12341 ± 1061 | −42.6 ± 8 | 0.0007 |
| 1.2 ($8 \times 10^{-6}$) | 10086 ± 701 | −53.1 ± 7 | <0.0001 |
| 1.5 ($10^{-5}$) | 10202 ± 915 | −52.6 ± 9 | <0.0001 |

Figure 6:
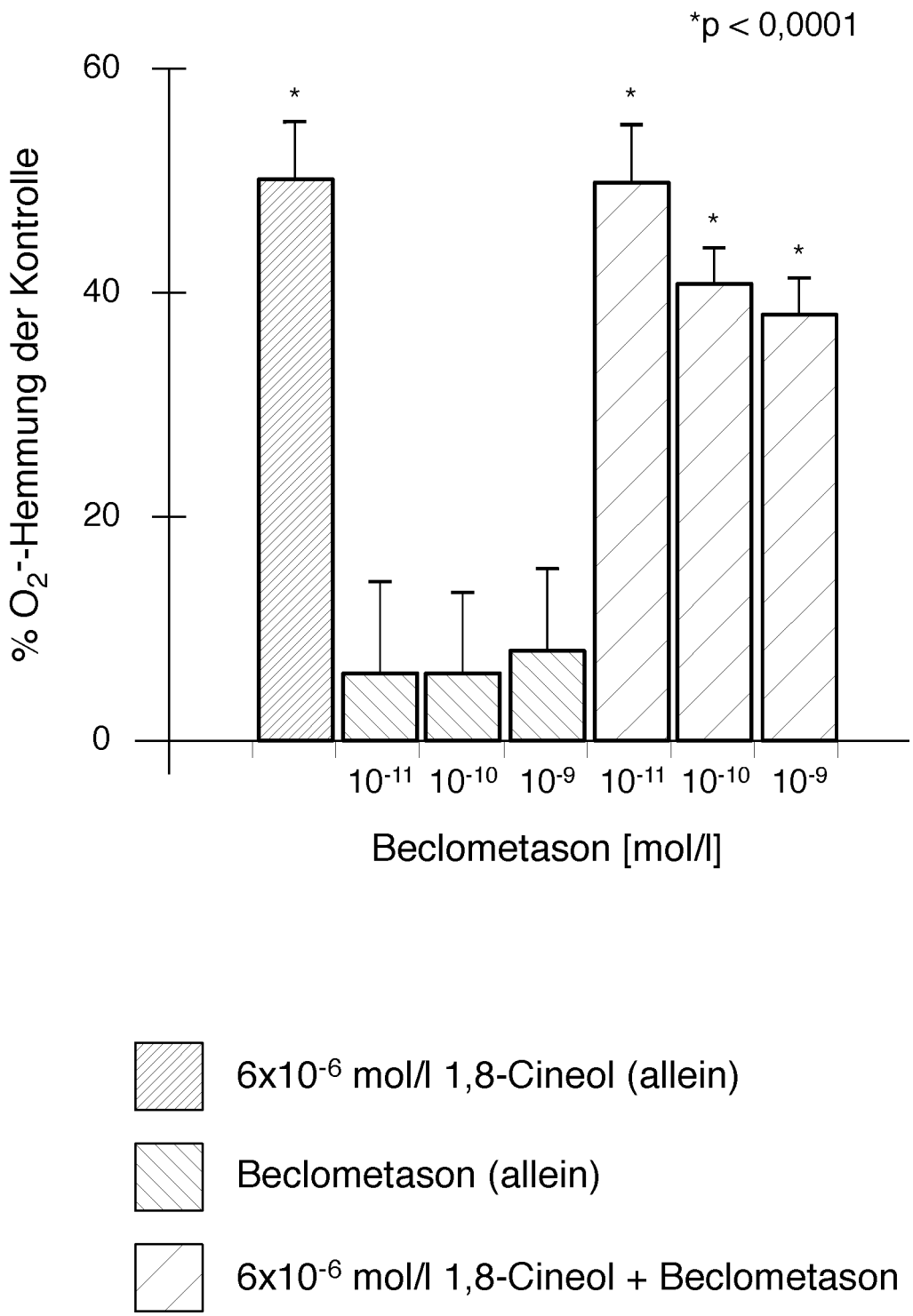
FIG. 6 illustrates the effect on $O_2^-$—inhibition provided by beclometasone (alone), 1,8-cineol (alone) and their combination.
Figure 7:
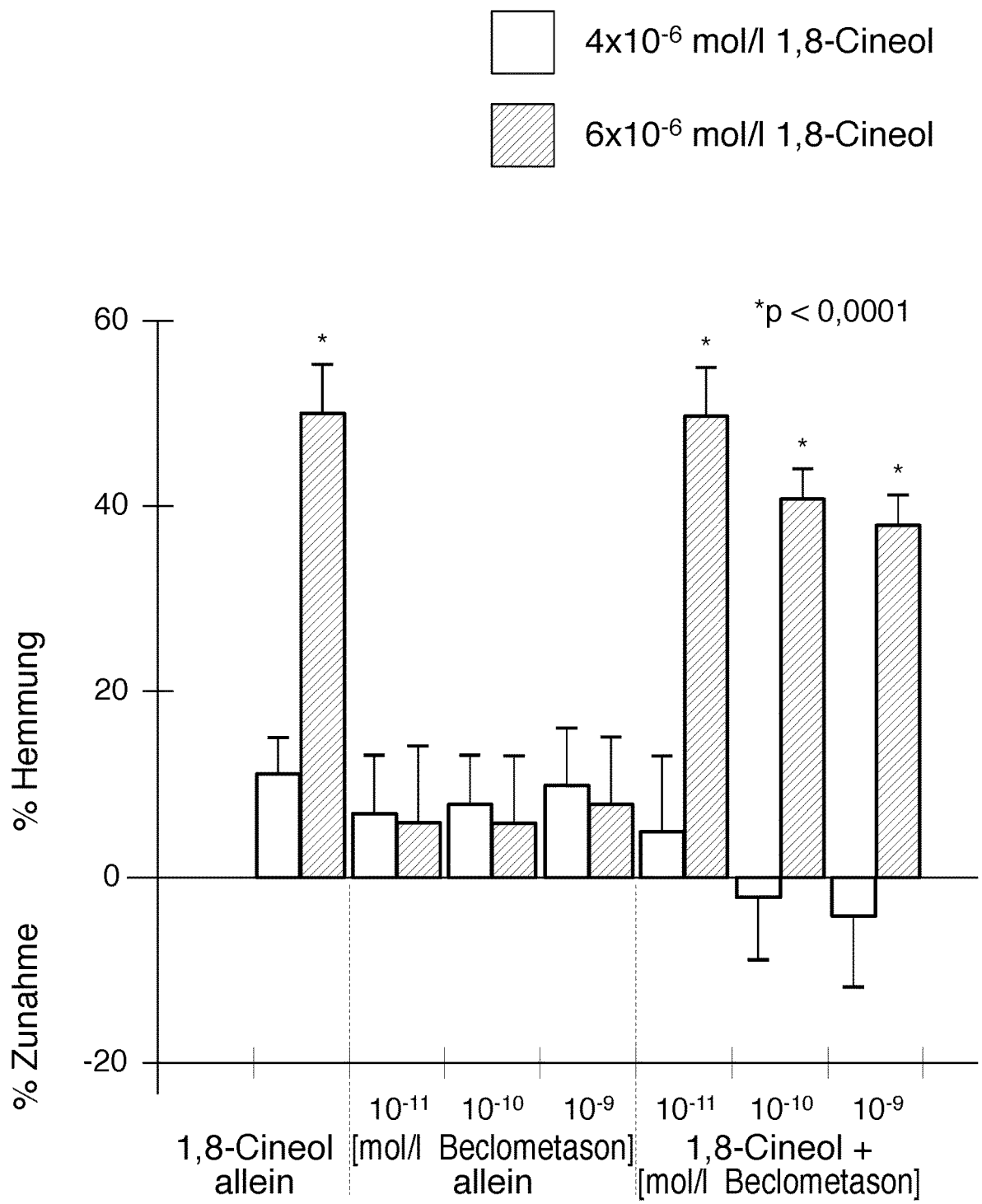
FIG. 7 provides data illustrating that the activity of 1,8-cineol is weakened by the properties of beclometasone.

Effect of an Optimum Concentration (0.9 μg/ml) of 1,8-cineol+Beclometasone on the FCS-stimulated Production of Superoxides ($O_2^-$) in Normal Monocytes A therapeutically relevant borderline concentration of 1,8-cineol $6 \times 10^{-6}$ mol/l (0.9 mg/ml) was determined as lowest antioxidatively active concentration for 1,8-cineol, and this concentration inhibited the $O_2^-$ production significantly (−50.2±5%, <0.0001). In this experimental series, too, beclometasone $10^{-11}$ to $10^{-9}$ mol/l on its own had no detectable effect on the $O_2^-$ production (see Table 6). Co-incubation of 1,8-cineol+beclometasone $10^{-11}$ mol/l inhibited the $O_2^-$ production (−49.9±5%, p<0.0001), and this effect is comparable (p=0.9215) to the effect of 1,8-cineol on its own. With increasing concentration of beclometasone ($10^{-9}$ mol/l) in the presence of 1,8-cineol, the antioxidative action tends to decrease, reaching −38.1±3% (p<0.0001) (see FIG. 6). Statistical analyses show that the inhibition of the $O_2^-$ production by 1,8-cineol+beclometasone $10^{-10}$ mol/l (−40.9±3%) is significantly weaker (p<0.0001) compared to 1,8-cineol on its own. The same also applies to 1,8-cineol+beclometasone $10^{-9}$ mol/l. Also, compared to 1,8-cineol+beclometasone $10^{-11}$ mol/l, the slightly decreasing inhibition of the $O_2^-$ production in the presence of higher doses of beclometasone for 1,8-cineol+beclometasone $10^{-10}$ mol/l (p=0.0165) and 1,8-cineol+beclometasone $10^{-9}$ mol/l (p=0.0053) is significant. These data show that the activity of 1,8-cineol is weakened by the properties of beclometasone ($10^{-10}$ and $10^{-9}$ mol/l) and that in the combination with beclometasone the leading role of the antioxidative activity is mediated by 1,8-cineol—without 1,8-cineol it cannot be detected in this combination (see FIG. 7).

TABLE 5

Effect of 1,8-cineol (0.6 μg/ml) and beclometasone ("becl.") on the FCS-stimulated superoxide production of normal human monocytes in vitro

| mol/l | n | $O_2^-$ (nmol/ml) | Percent of control | p-Value |
|---|---|---|---|---|
| spontaneous | 15 | 9294 ± 511 | — | — |
| FCS 10% | 15 | 17843 ± 940 | — | <0.0001 |
| 1,8-cineol $4 \times 10^{-6}$ | 15 | 16323 ± 1069 | −9 ± 6 | 0.2717 |
| becl. $10^{-11}$ | 14 | 16562 ± 1081 | −7 ± 6 | 0.4581 |
| becl. $10^{-10}$ | 15 | 16445 ± 903 | −8 ± 5 | 0.2998 |
| becl. $10^{-9}$ | 15 | 16052 ± 969 | −10 ± 6 | 0.1466 |
| 1,8-cineol + becl. $10^{-11}$ | 15 | 16867 ± 1399 | −5 ± 8 | 0.4186 |
| 1,8-cineol + becl. $10^{-10}$ | 15 | 18190 ± 1345 | +2 ± 7 | 0.7557 |
| 1,8-cineol + becl. $10^{-9}$ | 15 | 18659 ± 1555 | +4 ± 8 | 0.8519 |

Summary

The present results of the study show that a frequently employed inhalative steroid such as beclometasone does not inhibit and at a no longer therapeutically relevant high concentration ($10^{-6}$ mol/l) even significantly increases the stimulated production of $O_2^-$ radicals in monocytes. In contrast, the production of $O_2^-$ radicals is inhibited by therapeutically relevant concentrations of 1,8-cineol by about 50%. Accordingly, for the first time, the present study now shows that the strong inhibition of the production of $O_2^-$ radicals by therapeutic concentrations of 1,8-cineol in combination with beclometasone can be demonstrated and provides an advantage which cannot be mediated in an isolated manner by the inhalative steroid alone. This is not a purely additive effect but the mediation of the effect of 1,8-cineol on the combination of 1,8-cineol and beclometasone, without it being possible to detect an independent antioxidative effect of beclometasone.

The lack of any indication of an inhibition of the formation of $O_2^-$ radicals by beclometasone is presumably indicative of the stimulation of $O_2^-$ radicals found for higher, not therapeutically relevant concentrations of beclometasone. The results show that there is an interaction between beclometasone and 1,8-cineol which, at high doses of beclometasone, decreases the potent action of 1,8-cineol in a negative-synergistic manner. This is evidenced by the fact that 1,8-cineol on its own has a significantly stronger antioxidative action than in combination with beclometasone, and that even the activity of 1,8-cineol+beclometasone decreases significantly at increasing concentrations of beclometasone compared to a combination with a smaller beclometasone concentration.

Besides, further investigations show that fluticasone, too, induces the production of $O_2^-$ radicals, and that this takes place via an inhibition of superoxide dismutase, which metabolizes $O_2^-$ to $H_2O_2$. These effects also increase with increasing steroid receptor binding capability, and the present studies therefore suggest that inhaled steroids are at least not capable of developing any antioxidative action via the inhibition of $O_2^-$ radicals and very likely do not at all act as antioxidants. As far as this is concerned, the investigations show that 1,8-cineol, at least with respect to its surprising superior antioxidative action compared with the steroids used to date, mediates an advantageous, hitherto underestimated activity profile in the respiratory tract.

This alone is the reason for the additional therapy with 1,8-cineol of inflammatory respiratory disorders and makes a long-term therapy particularly recommendable. Since the development of COPD treated with ICS is delayed owing to a reduction of exacerbations, but still progresses when treated with a combined therapy, the lack of antioxidative activity in the medication currently available may play an essential role here. The progression of COPD is accelerated in particular by smoking cigarettes, which leads to a high deposition of inhaled $O_2^-$ radicals in the respiratory tract, which radicals can obviously not be inactivated by ICS or a combined therapy with LABA plus ICS, or the therapy is not sufficiently protectively active with respect to epithelial cells of the respiratory tract and macrophages, and it is therefore conceivable that the pathogenic stimulus persists and contributes to the progression of the respiratory disorder.

Another novel aspect of the present invention is the systemic inflammation, hitherto underestimated, in COPD, which inflammation is induced by smoking cigarettes, but also by the severity of the disorder. As far as this is concerned, the inhalative local therapy is presumably not sufficient to actually control the course of COPD. Likewise, the present data may also explain the lack of any effects of a systemic therapy of COPD with prednisolone which, in the presence of a nicotine-induced steroid resistance, promotes inflammation prooxidatively. Accordingly, in the future a new importance may be attributed to the substance 1,8-cineol. Moreover, owing to a confirmed local and systemic inflammatory reaction, COPD cannot be treated satisfactorily by an inhalative combined therapy alone, so that further foundations for new core statements with respect to the active compound 1,8-cineol are increasingly being developed by the external support of worldwide research efforts, which will have to be implemented in an appropriate manner.

In summary, the present data open up a very current and hitherto underestimated perspective which helps in the understanding of the novel range of indications for 1,8-cineol on a local level in spite of systemic administration. At the same time, this also provides new options as the compatibility has to be looked at as a consequence of interactions with different comedications. The adopted procedure will help in the correct assessment of the substance 1,8-cineol with respect to its action and the clinical use for respiratory disorders that can be derived therefrom.

TABLE 6

Additive effect of 1,8-cineol (0.9 µg/ml) and beclometasone ("becl.") on the FCS-stimulated superoxide production of normal human monocytes in vitro

| mol/l | n | $O_2^-$ (nmol/ml) | Percent of control | p-Value |
|---|---|---|---|---|
| spontaneous | 11 | 11050 ± 1102 | — | — |
| FCS 10% | 11 | 18778 ± 1178 | — | 0.0009 |
| 1,8-cineol $6 \times 10^{-6}$ | 11 | 9347 ± 494 | −50.2 ± 5 | <0.0001 |
| becl. $10^{-11}$ | 11 | 17639 ± 1372 | −6 ± 8 | 0.3088 |
| becl. $10^{-10}$ | 11 | 17577 ± 1191 | −6 ± 7 | 0.5545 |
| becl. $10^{-9}$ | 12 | 17338 ± 1305 | −8 ± 7 | 0.5767 |
| 1,8-cineol + becl. $10^{-11}$ | 11 | 9395 ± 493 | −49.9 ± 5 | <0.0001 |

TABLE 6-continued

Additive effect of 1,8-cineol (0.9 µg/ml) and beclometasone ("becl.") on the FCS-stimulated superoxide production of normal human monocytes in vitro

| mol/l | n | $O_2^-$ (nmol/ml) | Percent of control | p-Value |
|---|---|---|---|---|
| 1,8-cineol + becl. $10^{-10}$ | 11 | 11099 ± 386 | −40.9 ± 3 | <0.0001 |
| 1,8-cineol + becl. $10^{-9}$ | 11 | 11626 ± 369 | −38.1 ± 3 | <0.0001 |

The invention claimed is:

1. A method of treating a human suffering from a respiratory disorder, the method comprising the step of administering to the human a combination therapeutic comprising:
   (1) firstly, at least one systemically administered monoterpene, wherein the monoterpene is 1,8-cineol, and
   (2) secondly, at least one topically administered dose of a respiratory therapeutic, wherein the topically administered respiratory therapeutic is an inhalative respiratory therapeutic selected from the group consisting of corticosteroids,
wherein administering the combination therapeutic serves for reducing the dose of the topically administered inhalative respiratory therapeutic in the treatment of a respiratory disorder.

2. The method as claimed in claim 1, wherein the combination therapeutic is in the form of a kit.

3. The method as claimed in claim 1, wherein the respiratory disorders to be treated are bronchopulmonary disorders.

4. The method as claimed in claim 1, wherein the monoterpene is present in an oral administration form.

5. The method as claimed in claim 1, wherein the monoterpene is present in the form of capsules or in the form of an oral enteric preparation which does dissolve in the small intestine.

6. The method as claimed in claim 1, wherein the monoterpene is administered in daily doses of from 100 to 2000 mg/day or wherein the 1,8-cineol is employed in the form of enteric capsules, which dissolve in the small intestine, in daily doses of from 100 to 2000 mg/day.

7. The method as claimed in claim 1, wherein the respiratory therapeutic to be administered topically, by inhalation, is a corticosteroid selected from the group consisting of beclometasone, mometasone, budesonide, flunisolide, fluticasone, triamcinolone and their physiologically acceptable derivatives, salts and esters, and mixtures as well as combinations thereof.

8. The method as claimed in claim 1, wherein the bronchopulmonary disorder is an inflammatory or non-inflammatory disorder of the upper or lower respiratory tract.

9. The method as claimed in claim 1, wherein the bronchopulmonary disorder is bronchial asthma or bronchitis.

10. The method as claimed in claim 1,
wherein the bronchopulmonary disorder is a chronic obstructive pulmonary disorder (COPD), a chronic obstructive bronchitis or a pulmonary emphysema.

11. The method as claimed in claim 1,
wherein the combination therapeutic serves for the synergistic enhancement of the activity of the at least one topically administered inhalative respiratory therapeutic in the treatment of respiratory disorders.

12. The method as claimed in claim 1,
wherein the combination therapeutic serves for the prophylactic treatment of respiratory disorders.

13. The method as claimed in claim 1,
wherein the inhalative respiratory therapeutic selected from the group consisting of corticosteroids is combined with at least one further inhalative respiratory therapeutic selected from the group consisting of (i) sympathomimetics; (ii) phosphodiesterase inhibitors; (iii) parasympatholytics; (iv) vagolytics; and (v) anticholinergics; and mixtures as well as combinations thereof.

14. The method as claimed n claim 1,
wherein the activity of the at least one topically administered inhalative respiratory therapeutic is enhanced due to the combined administration of the monoterpene 1,8-cineol.

15. The method as claimed in claim 1,
wherein the topically administered corticosteroid exhibits an anti-inflammatory or antioxidative activity and the anti-inflammatory or antioxidative activity is enhanced due to the combined administration of the monoterpene 1,8-cineol.

16. A method of enhancing the efficiency of treating a human suffering from a respiratory disorder,
the method comprising the step of administering to the human a combination therapeutic comprising:
(1) firstly, at least one systemically administered monoterpene, wherein the monoterpene is 1,8-cineol, and
(2) secondly, at least one topically administered respiratory therapeutic, wherein the topically administered respiratory therapeutic is an inhalative respiratory therapeutic selected from the group consisting of corticosteroids;
wherein administering the combination therapeutic involves administering a reduced dosage of the topically administered respiratory therapeutic and obtaining an enhanced activity of the topically administered inhalative respiratory therapeutic due to the combined administration of the monoterpene, 1,8-cineol.

17. A method of enhancing the efficiency of treating a human suffering from a respiratory disorder,
the method comprising the step of administering to the human a combination therapeutic comprising:
(1) firstly, at least one systemically administered monoterpene, wherein the monoterpene is 1,8-cineol,
wherein the monoterpene is present in the form of capsules or in the form of an oral enteric preparation which does dissolve in the small intestine and wherein the monoterpene is administered in daily doses of from 100 to 2000 mg/day, and
(2) secondly, at least one topically administered respiratory therapeutic, wherein the topically administered respiratory therapeutic is an inhalative respiratory therapeutic selected from the group consisting of corticosteroids
selected from the group consisting of beclometasone, mometasone, budesonide, flunisolide, fluticasone, triamcinolone and their physiologically acceptable derivatives, salts and esters, and mixtures as well as combinations thereof;
thereby reducing the dose of the topically administered inhalative respiratory therapeutic due to the combined administration of the monoterpene 1,8-cineol and thereby enhancing the activity of the topically administered inhalative respiratory therapeutic due to the combined administration of the monoterpene 1,8-cineol.

* * * * *